(12) United States Patent
Gorenstein et al.

(10) Patent No.: US 8,165,820 B2
(45) Date of Patent: Apr. 24, 2012

(54) METHODS AND APPARATUS FOR PERFORMING RETENTION-TIME MATCHING

(75) Inventors: Marc V. Gorenstein, Needham, MA (US); Scott J. Geromanos, Middletown, NJ (US); Jeffrey Cruz Silva, Beverly, MA (US); Guo-Zhong Li, Westborough, MA (US)

(73) Assignee: Waters Technologies Corporation, Milford, MA (US)

( * ) Notice: Subject to any disclaimer, the term of this patent is extended or adjusted under 35 U.S.C. 154(b) by 481 days.

(21) Appl. No.: 11/916,322

(22) PCT Filed: Jun. 5, 2006

(86) PCT No.: PCT/US2006/021919
§ 371 (c)(1),
(2), (4) Date: Jun. 10, 2009

(87) PCT Pub. No.: WO2006/133191
PCT Pub. Date: Dec. 14, 2006

(65) Prior Publication Data
US 2011/0184648 A1 Jul. 28, 2011

Related U.S. Application Data

(60) Provisional application No. 60/687,057, filed on Jun. 3, 2005.

(51) Int. Cl.
G06F 19/00 (2006.01)
(52) U.S. Cl. .............. 702/19; 702/27; 702/30; 250/282; 250/559.4; 250/559.44
(58) Field of Classification Search .............. 702/19–23, 702/27, 30; 250/282, 559.4, 559.44
See application file for complete search history.

(56) References Cited

U.S. PATENT DOCUMENTS

2003/0129760 A1 7/2003 Aguilera et al.

FOREIGN PATENT DOCUMENTS

| JP | 2002110081 | | 4/2002 |
|----|------------|----|--------|
| WO | 2004049385 | | 6/2004 |
| WO | 2005113830 | A2 | 12/2005 |

(Continued)

OTHER PUBLICATIONS

European Search Report "EESR" for EP 06 772289.2, cf Form 1507, dated Aug. 19, 2010.
Japanese Translation of Notice of Rejection for Japan Patent Application No. 2008-514969, dated Jul. 5, 2011.

(Continued)

Primary Examiner — Drew A Dunn
Assistant Examiner — Hien Vo
(74) Attorney, Agent, or Firm — Muirhead and Saturnelli, LLC

(57) ABSTRACT

A method for matching a precursor ion with one or more related product ions includes providing input data sets obtained from sample injections, each of the data sets including a precursor ion and one or more product ions, normalizing the input data sets in accordance with a single retention time for the precursor ion, determining which product ions are within a predetermined retention time window with respect to the single retention time, and, if a product ion is within the predetermined retention time window for a specified number of the input data sets, determining that the product ion is related to the precursor having the single retention time. An apparatus for analyzing a sample includes a chromatography module, a mass-spectrometry module in communication with the chromatography module, and a control unit in communication with the chromatography module and the mass-spectrometry module.

31 Claims, 20 Drawing Sheets

FOREIGN PATENT DOCUMENTS

| | | |
|---|---|---|
| WO | 2005114930 A2 | 12/2005 |
| WO | 2006133109 A1 | 12/2006 |

OTHER PUBLICATIONS

Lin et al, Prediction of relative retention times of triacylglycerols in non-aqueous reversed-phase high-performance liquid chromatography, Journal of Chromatography A, May 29, 1998, pp. 43-49, vol. 808, Elsevier Science.

Beer et al, Improving large-scale protemics by clustering of mass spectrometry data, Proteomics, 2004, pp. 950-960, vol. 4, Wiley-VCH Verlag GmbH & Co. KGaA, Weinheim.

Silva, et al, Quantitive Proteomic Analysis by Accurate Mass Retention Time Pairs, Analytical Chemistry, Apr. 1, 2005, pp. 2187-2200, vol. 77, American Chemical Society.

METHODS AND APPARATUS FOR PERFORMING RETENTION-TIME MATCHING

TECHNICAL FIELD

The invention generally relates to analyses of compounds, and, more particularly, to instruments and methods for polypeptide analyses.

BACKGROUND INFORMATION

Proteomics generally refers to studies involving complex mixtures of proteins derived from biological systems. Proteomic studies often focus on identification of proteins or determination of changes in the state of a biological system. Identification and quantification of proteins in complex biological samples is a fundamental problem in proteomics.

Liquid chromatography coupled with mass spectrometry (LC/MS) has become a fundamental tool in proteomic studies. Separation of intact proteins or of their proteolyzed peptide products by liquid chromatography (LC) and subsequent analysis by mass spectrometry (MS) forms the basis of many common proteomic methodologies. Methods that measure changes in the expression level of proteins are of great interest as they can form the basis of biomarker discovery and clinical diagnostics.

Rather than directly analyzing intact proteins, proteins of are typically digested to produce a specific set of proteolytic peptides. The resulting peptides are then often characterized via LC/MS analysis. A common enzyme used for digestion is trypsin. In tryptic digestion, the proteins present in a complex mixture are cleaved to produce peptides as determined by the cleavage specificity of the proteolytic enzyme. From the identity and concentration of the observed peptides, available algorithms serve to identify and quantify the proteins in the sample.

In LC/MS analysis, the peptide digest is first separated and analyzed by LC separation followed by MS analysis. Ideally, the mass of a single peptide, measured with sufficient accuracy, provides a unique identification of the peptide. In practice, however, achieved mass accuracies typically are on the order of 10 ppm or larger. In general, such mass accuracy is not sufficient to uniquely identify a peptide using the mass measurement alone.

For example, in the case of a mass accuracy of 10 ppm, on the order of 10 peptide sequences are identified in a search of a typical database of peptides sequences. This number of sequences would increase significantly if search restraints on mass accuracy were lowered, or searches for chemical or post-translational modifications, losses of $H_2O$ or $NH_3$, and point mutations were allowed, for example. Thus, if a peptide's sequence is modified by either a deletion or substitution, use of only the precursor's mass for identification of the petite will lead to a false identification. A further complication arises from the possibility that two peptides can have the same amino acid composition but have different sequences.

In the case of peptide precursors, product fragments can be obtained by fragmentation at a single peptide bond in the precursor. Such a single fragmentation produces two sub-sequences. The fragment containing the peptide's C-terminal, if ionized, is termed a Y-ion, and the fragment containing the peptide's N-terminal, if ionized is termed a B-ion.

Proteins are often identified by comparing analysis data to a database that associates protein identities with information about fragments of the proteins, such as masses of the fragments. For example, if a theoretical peptide mass from a database lies within a mass search window of the mass of a precursor measured in the data, it is deemed a hit.

The search can provide a list of possible matching peptides found in the database. These possible matching database peptides may or may not be weighted by statistical factors. The possible outcomes of such a search are that no possible matching database peptides are identified, one possible matching database peptide is identified, or more than one possible matching database peptide are identified. The higher the resolution of the MS, assuming proper instrument calibration, the smaller the ppm threshold, and consequently, the fewer the false identifications. If there are one or more matches to the peptides in the database, peptide-fragment ion data may be used to validate a match.

During a search, multiple charge states and multiple isotopes can be searched. Further, empirically produced confidence rules can be applied to help identify valid matches.

SUMMARY OF THE INVENTION

Some embodiments of the arise from the realization that multiple chromatographic injections of a sample are useable to distinguish precursors and related product ions by exploiting a retention-time shift exhibited by precursors relative to one another from injection-to-injection. Such shifts are induced, for example, even by small changes in temperature, solvent composition, and other chromatographic-separation parameters. Generally, the retention times of different precursors will shift differently from injection-to-injection, even if each injection uses substantially the same method and portions of the same sample. Optionally, intentional and/or random perturbations are used to cause the shifts.

Some embodiments relate to generation and/or use of a catalog of protein profiles developed through observation of retention-time shifts. In some embodiments, observation of only a few fragments of a compound provides accurate detection and/or quantification of that compound in a sample.

Accordingly, one embodiment of the invention features a method for matching a precursor ion with one or more related product ions. The method includes providing input data sets obtained from sample injections, each of the data sets including at least one precursor ion and one or more product ions, normalizing the input data sets in accordance with a single retention time for the precursor ion, determining which product ions are within a predetermined retention time window with respect to the single retention time, and, if a product ion is within the predetermined retention time window for a specified number of the input data sets, determining that the product ion is related to the precursor.

Another embodiment of the invention features an apparatus for analyzing a sample. The apparatus includes a chromatography module, a mass-spectrometry module in communication with the chromatography module, and a control unit in communication with the chromatography module and the mass-spectrometry module. The control unit includes at least one processor and a memory for storing instructions executed by the processor. The instructions cause the processor to perform actions such as those included in the above-described method.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DESCRIPTION

Figure 1:
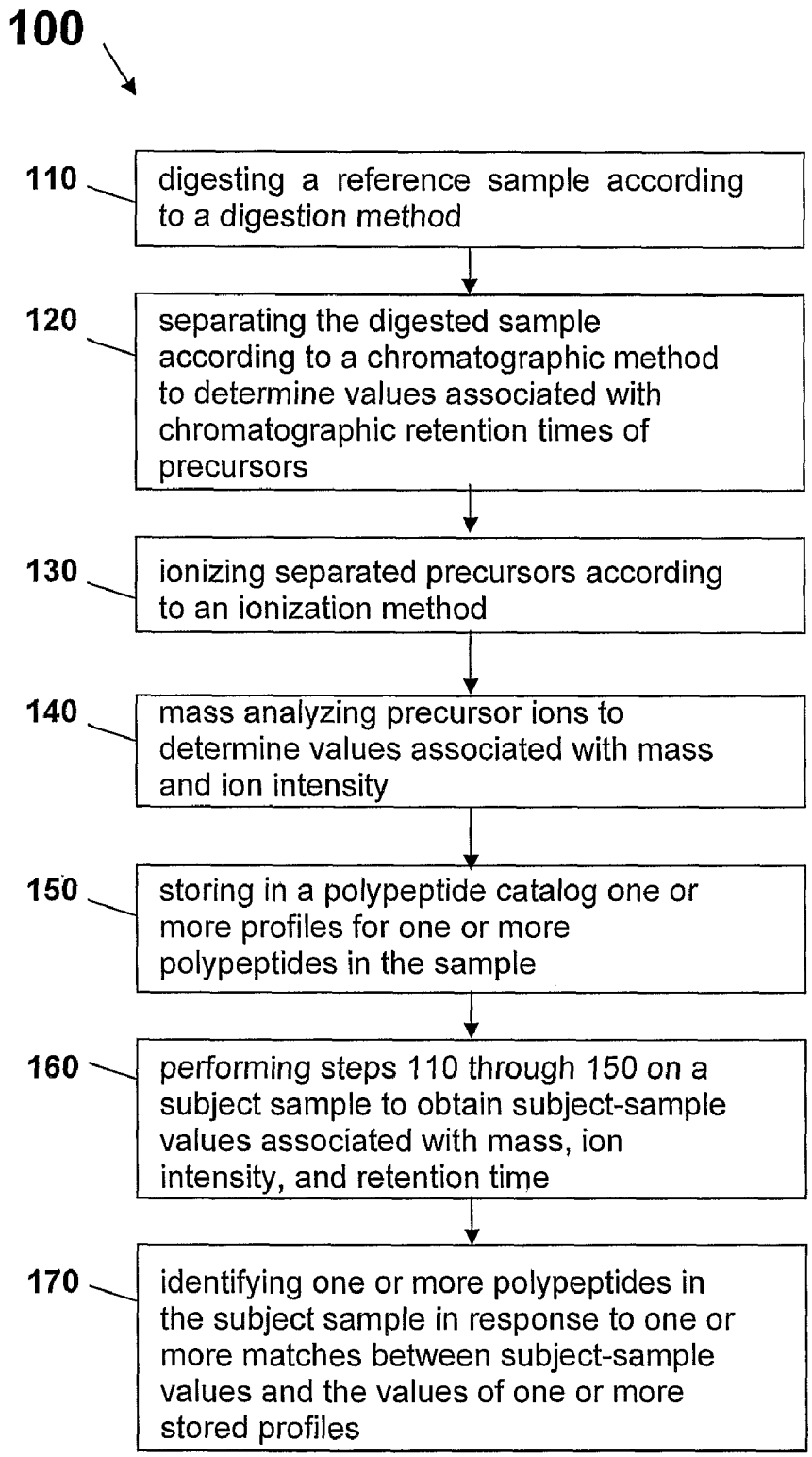
FIG. 1 is a flow diagram of a method for performing chemical analyses of compounds, in accordance with one embodiment of the invention.

As used herein, the following terms generally refer to the indicated meanings:

Protein—a specific primary sequence of amino acids assembled as a single polypeptide.

Peptide—a specific sequence of amino acids assembled as a single polypeptide contained within the primary sequence of a protein.

Tryptic peptides—peptides generated from a protein sequence that result from enzymatic cleavage of the protein by trypsin. In the ensuing description, digest peptides are referred to as tryptic peptides for convenience. It should be understood, however, that embodiments of the present invention apply to other peptide digestion techniques. Moreover, the term "digestion" is used herein to refer generally to any suitable method for degrading or cleaving a polypeptide, including, for example, the use of cellular enzymes (proteases) and intramolecular digestion. The term "proteolytic," as used herein, refers to any enzyme which digests or lyses large proteins into smaller sections or amino acids.

Precursor peptides—tryptic peptides (or other protein cleavage products) that are generated using a protein-cleavage protocol. The precursors are optionally separated chromatographically and passed to a mass spectrometer. An ion source ionizes these precursor peptides to typically produce a positively charged, protenated form of the precursor. The mass of such positively charged protenated precursor ion is herein referred as the "mwHPlus" or "MH+" of the precursor. In the following, the term "precursor mass" refers generally to the protenated, mwHPlus or MH+ mass of the ionized, peptide precursor.

Fragments—Multiple types of fragments can occur in LC/MS analyses. In the case of tryptic peptide precursors, fragments can include polypetide ions that are produced from collisional fragmentation of the intact peptide precursors and whose primary amino acid sequence is contained within the originating precursor peptide. Y-ions and B-ions are examples of such peptide fragments. Fragments of tryptic peptides can also include immonium ions, functional groups such as a phosphate ion ($PO_3$), mass tags cleaved from a specific molecule or class of molecules, or "neutral loss" of water ($H_2O$) or ammonia ($NH_3$) molecules from the precursor.

Y-ions and B-ions—If a peptide fragments at the peptide bond, and if a charge is retained on the N terminal fragment, that fragment ion is termed a B-ion. If the charge is retained on the C terminal fragment, the fragment ion is termed a Y-ion. A more comprehensive list of possible fragments and their nomenclature is provided in Roepstorff and Fohlman, Biomed Mass Spectrom, 1984; 11(11):601 and Johnson et al, Anal. Chem 1987, 59(21): 2621:2625.

Retention time—in context, typically refers to the point in a chromatographic profile at which an entity reaches its maximum intensity.

Ions—each peptide typically appears in an LC/MS analysis as an ensemble of ions due to the natural abundance of the isotopes of the constituent elements. An ion has a retention time and an m/z value. The mass spectrometer (MS) detects only ions. The LC/MS technique produces a variety of observed measurements for every detected ion. This includes: the mass-to-charge ratio (m/z), mass (m), the retention time, and the signal intensity of the ion, such as a number of ions counted.

MwHPlus—The neutral, monoisotopic mass of the peptide plus the weight of one proton, 1.007825 amu.

Generally, an LC/MS analysis optionally provides an empirical description of a peptide in terms of its mass, charge, retention time and total intensity. When a peptide elutes from the chromatographic column, it elutes over a specific retention time period and reaches its maximum signal at a single retention time. After ionization and (possible) fragmentation, the peptide appears as a related set of ions. The different ions in the set correspond to different isotopic compositions and charges of the common peptide. Each ion within the related set of ions produces a single peak retention time and peak shape. Since these ions originate from a common peptide, the peak retention time and peak shape of each ion is identical, within some measurement tolerance. The MS acquisition of each peptide produces multiple ion detections for all isotopes and charge states, all sharing the same peak retention-time and peak shape within some measurement tolerance.

In an LC/MS separation, a single peptide (precursor or fragment) produces many ion detections, which appears as a cluster of ions, at multiple charge states. Deconvolution of these ion detections from such a cluster, indicates the presence of a single entity of a unique monoisotopic mass, at a specific retention time, of a measured signal intensity, in a charge state.

Protein Database—In some embodiments of the present invention, an analyst utilizes a database of proteins. In a typical database, each included protein is described by its primary sequence of amino acids. An analyst might choose a database that is intended to closely match proteins under study. For example, an *E. Coli* database could be compared to data obtained from a cell lycate of *E. Coli*. Similarly, a human serum database could be compared to data obtained from human serum. A user could choose a subset database. A user could choose a superset database, such as all proteins listed in the SwissProt database produced by the Swiss-Prot groups at the Swiss Institute of Bioinformatics (SIB) and the European Bioinformatics Institute (EBI). A user could choose a data a base that contains simulated proteins, described by random sequences of amino acids. Such random databases are used in control studies to evaluate or calibrate protein identification systems and search algorithms. A user could choose a database that combines both naturally occurring and artificial sequences. From the protein database, one can infer from each sequence, the sequence and masses of tryptic precursor ions, Y- and B-ions, and other possible fragment ions that would result from those precursors.

FIG. 1 is a flow diagram of a method 100 for performing chemical analyses of compounds. The method 100 includes digesting 110 one or more compounds of a reference sample into component fragments of the compounds, separating 120 the components, ionizing 130 and mass analyzing 140 at least some of the separated components, and storing 150 in a catalog of profiles a profile of at least one compound in the sample.

The method optionally includes repeating 160 on a subject sample the steps of digesting 110, separating 120, ionizing 130 and mass analyzing 140, and identifying 170 the one or more compounds in the subject sample in response to a match between subject-sample analysis data and data stored in the profiles of the one or more compounds.

Preferably, for repeating 160 analysis steps on the subject sample, effectively the same pre-selected method(s) for digestion, chromatographic separation, and/or ionization are used for digesting 110, separating 120, ionizing 130, and mass analyzing 140 of the subject sample as used for the reference sample. Through use of substantially the same methods, subject-sample data is more accurately compared to a catalog of profiles to identify 170 compounds in the subject sample. Thus, an analyst optionally develops her own catalog using her own analytical instruments and analysis methods or recipes, and thus produces more reliably and easily obtains identifications than otherwise possible through use of generic databases.

Optionally, through use of substantially the same methods, catalogs prepared by different analysts in different laboratories are combined into master catalogs. These catalogs are then useable by other analysts to identify proteins obtained through substantially the same methods. Thus, for example, different labs or different instruments in the same lab, using substantially the same equipment and methods, may collaboratively produce catalogs of protein profiles. Such labs may also be users of such catalogs.

Some preferred uses of the method 100 are directed toward protein-related analyses. Thus, for convenience, the following description refers to proteins and related fragments, and utilizes examples of analyses of compounds that are polypeptides, such as proteins; in these examples, a protein is digested into component fragments that are precursor fragments of the protein. Precursors, in turn, are ionized to form precursor ions and optionally are themselves fragmented into product ions in preparation for mass analysis.

Although the description focuses on examples related to polypeptides, such examples are not intended to limit the scope of the invention to analyses of polypeptides; one having ordinary skill in the chemical-analysis arts will recognize that principles of the invention are applicable to analyses of other chemical compounds.

Digesting 110 is accomplished via any suitable technique for cleaving proteins, including known techniques. For example, as described above, a protein is digested into precursor polypeptides or amino acids through use of one or more enzymes such as trypsin. Fragments of a protein or polypeptide are herein generally referred to as "precursors." Such a fragment is a precursor in the sense that it is optionally used in additional analyses subsequent to chromatographic separation. As described in more detail below, precursor fragments are optionally ionized and/or further fragmented into product fragments.

Separating 120 is accomplished by any suitable chromatographic-related technique, including known techniques such as reverse-phase chromatography, gel-permeation chromatography, size-exclusion chromatography, and electrophoresis. Separating 120 provides values associated with retention times of the proteins and/or precursors obtained from digesting 110 proteins in a sample.

In preparation for mass analyzing 140 the eluent of a chromatographic separation 120, the eluent from the separating 120 process is subjected to an ionizing 130 process. Any suitable ionizing 130 process is optionally used, including known techniques such as electrospray ionization and MALDI. During the ionizing 130 process, at least some of the precursors are ionized to form precursor ions. For example, a single protein molecule is digested 110 to form twenty precursor fragments, of which ten are ionized during ionizing 130. Optionally, as described in more detail below, precursors are further fragmented to obtain product ions to assist in the identification of associated precursors.

Mass analyzing 140 provides values associated with mass and values associated with ion intensity of the precursor ions. Mass analyzing 140 is performed via any suitable mass-analysis techniques, including known techniques. Such techniques include magnetic-sector spectrometry and time-of-flight spectrometry.

Information obtained from the above-described analysis is used to define one or more profiles for one or more associated proteins in the sample. A protein profile is defined by values associated with retention time, ion mass, and ion intensity of precursor ions associated with the protein. Optionally, the profile of the protein is also defined by the identity of the protein. Some preferred embodiments include product-ion data in profiles. Thus, the profile of the protein may also be defined by values associated with retention time, ion mass, and ion intensity of product ions associated with the precursors of the protein.

The profile is stored 150 in a catalog of profiles for later use in detecting, identifying and/or quantifying the protein in later analyzed subject samples. Optionally, the profiles are defined in an existing protein database by annotating the proteins listed in the database with values associated with retention time, ion mass, and ion intensity of precursor ions associated with the corresponding listed proteins.

Any suitable measure of ion-intensity value is used in the definition of profiles. For example a total number of ion counts in an LC/MS peak is suitably used, as will be understood by one having ordinary skill in the chemical-analysis arts.

The particular types of values used to define a protein profile optionally are varied, for example, to suit a particular need of an analyst. A profile is optionally defined, for example, with values of m/z and/or precursor charge state and/or other values as will be recognized by one having ordinary skill.

The analysis and profile definition process are optionally repeated, as desired. Thus, a catalog of protein profiles is developed that provides a convenient reference source for analysis of subject samples that include known and/or unknown proteins. The catalog optionally includes more than one profile for each of one or more proteins. Moreover, as described in more detail below, subject samples themselves optionally provide data for additional protein profiles. Examples of some protein profiles are described below with reference to FIG. 4 through FIG. 7.

Once a catalog includes a profile for a particular protein, that protein is available for detection, identification 170, and/or quantitation in a subject sample analyzed optionally by the same or sufficiently the same analysis steps described above. This approach provides sufficiently comparable analysis data for the protein in the subject sample to be accurately matched to the corresponding data in the profile in the catalog. A confirmed match with the precursor-related data in the profile confirms the detection of the protein in the subject sample. Optionally, a confirmed match with the product-related data in the profile confirms the detection of the protein in the subject sample. Moreover, the intensity data obtained from the subject sample, in comparison to the intensity data in the profile, from precursors and/or products optionally provides quantification of the protein in the subject sample.

A catalog is searched for possible matches in any suitable manner. For example, comparisons are iteratively made with each profile in a catalog until a best match, if any, is obtained. If a same LC method is used to generate a catalog and to analyze a subject sample, retention-time values of subject-sample precursor ions are directly comparable to profile values, using, for example, a pre-selected retention-time window. Product-ion retention times are optionally included in this comparison.

If different LC methods are used, such that retention-time values are less useful, comparison to mass-related values may still be used to associate subject-sample precursor-ion data with corresponding protein profiles.

Generally, the intensity values of precursors in a subject sample will be different than the values stored with a corresponding profile because of protein concentration differences. A scaling factor is optionally applied to provide effectively exact matches between subject-sample precursor ions and profile precursor ions. A determined scaling factor is optionally used for quantification of the protein in the subject sample.

Generally, if a protein has a higher concentration in a subject sample than it had in a reference sample that was used to define its profile, all precursors included in the profile will be observable in the subject sample. Conversely, if the subject sample concentration is lower relative to the profile, some profile precursor ions may be undetectable.

After a correspondence between a subject sample's precursor-ion data and a profile is obtained, the match is optionally confirmed though additional comparison steps. For example, an initial match based on comparisons of data for three precursors is optionally verified by comparing data for additional precursors and/or product ions. For example, a scale factor determined from the initial comparisons is usable to search for matches between values for the additional components of the profile. Thus, generally, additional available data should be consistent with a preliminary match to validate the preliminary match.

In some embodiments, data of a single precursor is used to obtain a match to a profile, provided that the match includes a match between retention-time values. Without retention-time matching, data of at least two precursor ions is preferably used. Often, good accuracy in matching is obtained through use of data of three precursor ions. With a confirmed match, the identity and concentration of the match protein are optionally indicated. Preferably, precursor ions having greatest intensity values are used to define profiles and for comparisons to those profiles. If product-ion data are included in the protein profile, and are observed in the sample, these ions can be matched to further confirm the identify of the protein in the sample.

Figure 2:
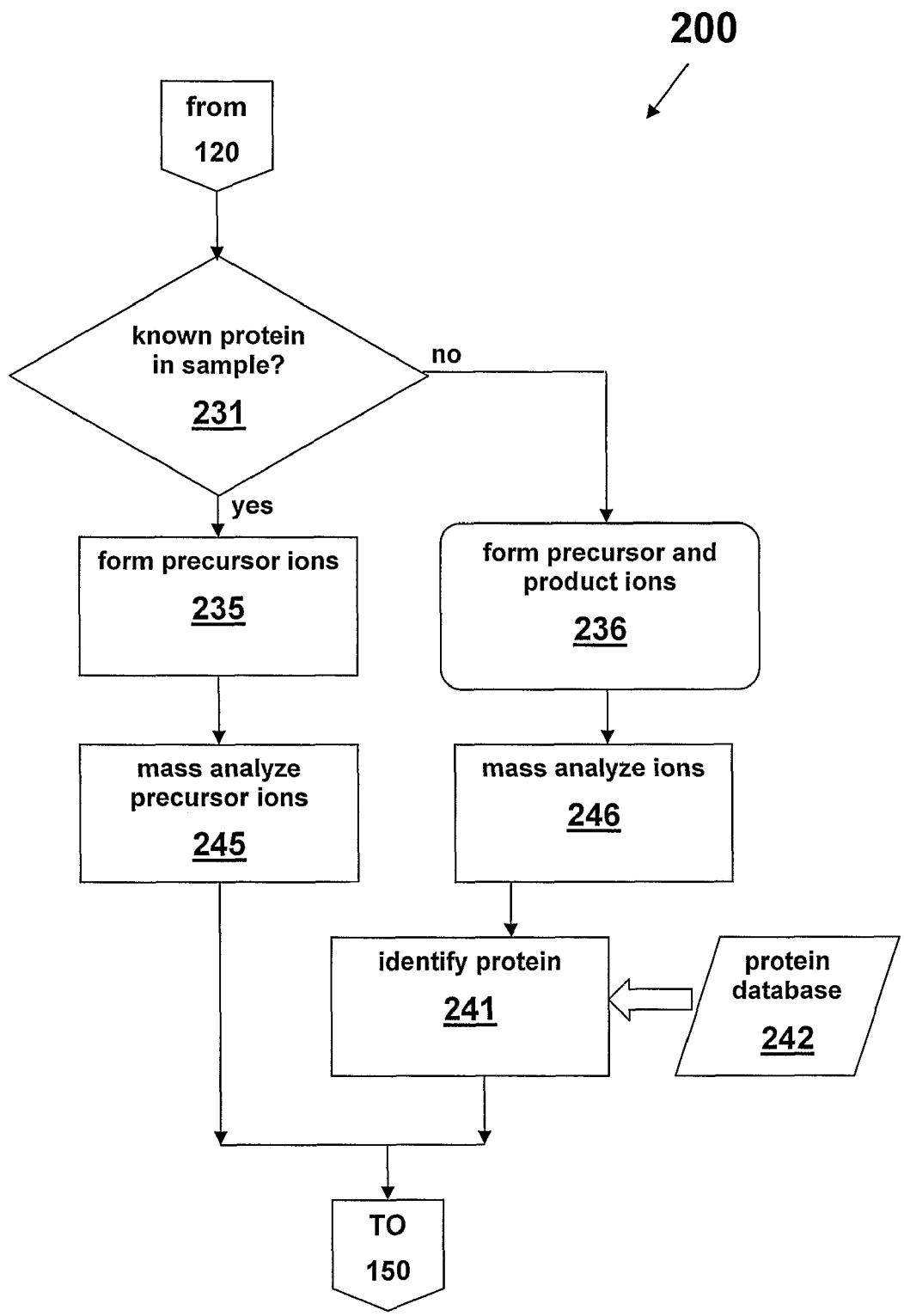
FIG. 2 is a partial flow diagram of a method that is related to the method of FIG. 1.

The reference sample optionally includes unknown and/or known proteins, and the method 100 optionally assists accurate identification of proteins in the reference sample in support of a definition of a profile for that protein. For example, FIG. 2 is a partial flow diagram of a method 200 for performing chemical analyses of compounds that is an alternative embodiment of the above-described method 100. The method 200 includes digesting 110, separating 120, and storing 150 a profile of at least one compound in the sample, as for the method 100.

For the processes of ionizing 130 and mass analyzing 140, the method 200 includes the following described more detailed steps. These steps provide different processing for unknown proteins and for known proteins. The different processing, as described below, provides reliable identification of unknown proteins in support of the definition of correct profiles.

In response to a decision 231 that a protein of interest has an identity that is known to an analyst, precursor ions are formed 235 from the known protein, the precursors are mass analyzed 245, and the protein profile is then optionally defined and stored 150 using the known identity and the precursor-ion data associated with the observed values related to retention time, ion mass, and ion intensity.

Optionally, if product ions are formed from the known protein precursors, the product ions are mass analyzed, and the protein profile is then optionally defined and stored 150 using the known identity and the product-ion data associated with the observed values related to retention time, ion mass, and ion intensity.

If the identity of the protein of interest in the sample is determined 231 to be unknown to the analyst, both precursor and product ions are optionally formed 236 from the protein, and both the precursor ions and product ions are mass analyzed 246. The product ions are used to validate identities of the precursor ions. The validated precursors, in turn, support reliable use of precursor data to identify the protein. For example, precursor data is used in a search of a pre-existing protein database 242. One suitable procedure that is optionally used to implement precursor validation is described in PCT Patent Application International Publication No. WO 2005/114930, published on Dec. 1, 2005, which is incorporated herein by reference.

Thus, if a polypeptide in the sample is an unidentified polypeptide, the method 200 optionally includes identifying the polypeptide by searching a pre-existing protein database 242 for a protein having precursors identified via the analysis. Suitable databases 242 are commercially or freely available, as known to one having ordinary skill in the protein analysis arts.

The database 242, for example, includes a list of proteins and, for each listed protein, associated tryptic peptides indicated by, for example, their precursor ion masses.

In one exemplary embodiment, the protein database 242 includes a collection of proteins and their theoretical peptide sequences. In this example, a protein in the sample is identified 241 by searching the databases' sequences for evidence of precursor and product ions that correspond to a theoretical peptide sequence. If a sufficient number of such masses are found in the data, and at a common retention time, then the peptide sequence is identified in the data. If, for example, this approach finds in the data one or more peptide sequences associated with a given protein, then the protein is taken to be identified 241 in the sample.

In some preferred implementations of the method 200, the data is gathered using an LC/MS system and a preselected database 242 (i.e., to accomplish steps 120, 236, 246, 241.) For example, as described in more detail with reference to FIGS. 9A and 9B, an eluent output by the liquid chromatograph is introduced into a mass spectrometer through an electrospray interface. Optionally, a first quadrupole of a triple-quadrupole MS instrument functions as an ion guide. An alternating voltage is applied to a collision cell of the instrument. Spectra are collected of precursors ions and of their fragment (product) ions, for example in an alternating fashion, as described below.

Preferably, both precursor ions and associated product ions are formed from the same precursor material obtained from the separating 120 process. In this manner, both precursor ions and associated product ions will have the same retention time data determined from the separating 120 process. Product ions may thus be relatively readily associated with the precursor from which they arose. Less desirably, two or more injections of a sample are performed, and precursor-ion and product-ion data are obtained from different injections.

Any suitable method, including known methods, may be used to obtain both precursor and product ions from a single sample injection. Such methods provide effectively simultaneous mass analysis of both precursor and product ions. For example, a portion of an eluted precursor is fragmented to form product ions, and the precursor and product ions are substantially simultaneously analyzed 246, either at the same time or, for example, in rapid succession.

As an alternative example, two or more alternating portions of the peak are used respectively for precursor and product analysis. A portion of a peak's precursor material is ionized and analyzed, and then a next portion is dissociated into product fragments that are analyzed. In one preferred embodiment, alternating portions of an eluting precursor are sampled to alternately obtain data for the precursor ion and its product ions. The obtained data permits reconstruction of a peak shape to permit measurement of an accurate retention time value for both the eluted precursor and its associated product. Moreover, for example, peak shape, width, and/or time of reconstructed peaks associated with precursor ions and with product ions are optionally compared to determine which product ions are associated with a particular product ion.

One approach to such alternating, effectively simultaneous analysis, is described in U.S. Pat. No. 6,717,130 to Bateman, et al. ("Bateman"), which is incorporated herein by reference and describes application of an alternating voltage to a collision cell to regulate fragmentation. Additional description of related features is provided below with reference to FIGS. 9A and 9B.

Thus, the technique described in the Bateman or other suitable technique uses retention-time observations to support the determination of which product ions are derived from a particular precursor. The product ions are associated with their precursor ion in response to matching retention-time values.

For example, a threshold retention-time difference is selected; if the difference in retention times of a product ion and a precursor ion is less than the threshold value, the product is determined to be derived from the precursor. For example, one suitable threshold value is equal to one tenth the retention-time peak width of the precursor ion.

The retention-time value of an ion is optionally defined as the time value of the peak maximum of the peak that was observed for that ion.

Once a catalog of protein profiles is generated, as described above, the catalog is optionally used to support accurate identification 170 of proteins in subject samples without referring to a pre-existing protein database. For example, a protein in a subject sample is optionally identified through a determination that the three most intense precursors of the protein—as listed in the profile of the protein—are appropriately present in the sample. The presence of the precursors in the data is determined by matching the retention-time values, mass values, and intensity-ratio values of the collected data with the values of the profile. Fewer or more precursors are optionally used to determine matches and/or other than the three most intense precursor ions may be utilized.

Use of the protein profiles provides a number of advantages over some prior identification methods. For example, a protein may be accurately identified even when present at relatively low concentration. A low concentration sample often provides little or no detectability of product ions. The corresponding protein profile, however, provides relatively reliable, accurate precursor data for comparison if the profile was developed from a sample having a relatively high concentration of the protein.

After identification of the protein, the identification is optionally confirmed by comparisons of additional data for other precursors and/or comparisons of product-ion data in the profile if expected to be present at an observable level. The concentration of the protein in the subject sample is optionally determined by comparisons to intensity-related data of the profile.

A catalog of protein profiles is optionally supplemented and/or updated upon analysis of additional reference and/or subject samples. For example, if the method 200 identifies a protein that is not present in the catalog, a profile of the protein is defined and stored 150 in the catalog. For example, if the method 200 observes a protein that already has a profile in the catalog, the existing data in the protein's profile may be supplemented or replaced with the newly acquired data. For example, a more reliable profile is possibly obtained if the protein was present at a greater concentration in the newly observed sample than existed for the prior sample that was used to define the profile. Thus, both reference samples and subject samples are usable by an analyst to build and update a catalog of profiles.

For example, each injection provides a potential new profile for each protein present in that sample. The catalog is optionally continuously updated, expanded and refined, as new injections are analyzed. For example, different samples may contain the same protein, but at different concentrations. In general, the best available profile of a protein is the one that has the highest intensities.

Thus, the analyst optionally commences with profiles obtained from a first sample injection, and systematically compares these profiles to all profiles present in a (possibly large) catalog of previously defined protein profiles. If the intensity associated with a profile in the injection exceeds the intensity associated with a matching existing profile in the catalog, then new data either supplements the data in the existing profile, or simply replaces the existing data in the profile.

As described above, if a protein profile obtained from an injection is not present in the catalog, then the protein profile is optionally added to the catalog of profiles. Optionally then, an initial catalog is empty and all subsequent injections are used to populate, refine, and/or expand the protein profiles in the catalog. In some alternative embodiments, a catalog includes one or more protein identities for profiles that have yet to include precursor-related data. The profiles are then defined with data as the proteins are observed in analyzed samples.

Figure 3:
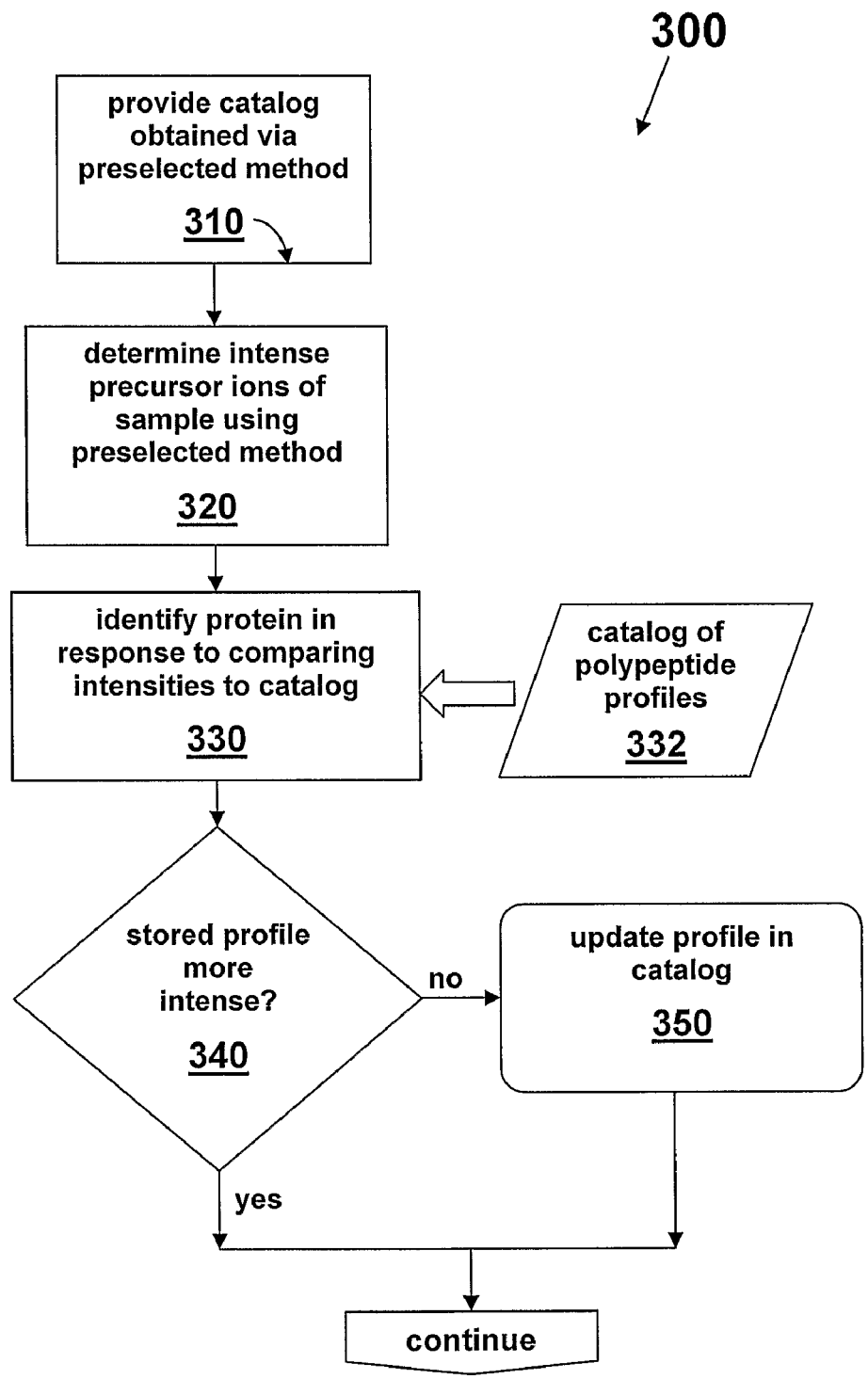
FIG. 3 is a flow diagram of a method for chemical analyses, in accordance with one embodiment of the invention.

FIG. 3 is a flow diagram of another method 300 for chemical analysis, which includes providing 310 a catalog 332 of protein profiles obtained through use of a pre-selected method and identifying 330 one or more unidentified proteins in response to a comparison between the catalog 332 and a determination 320 of intense precursor ions. If 340 the stored profile has lower intensity values than provided by a newly observed protein, the catalog is updated 350.

For example, one or more analysts develop the catalog 332 and one or more analysts then utilize the developed catalog 332 to detect, identify and/or quantify one or more proteins in a sample. The same or similar equipment is preferably used for sample analysis as was used to develop the catalog. The catalog can be obtained from similar equipment in different laboratories and generated by the same or different analysts. Catalogs obtained from the same or different equipment in the same or different laboratories can be combined to form a single or additional catalogs.

As mentioned, protein-profile data is also optionally used to quantify the concentration in a sample of a detected protein. For example, if the concentration of the protein was known or determined for the prior sample that was used to define the protein's profile, the profile optionally includes an indicator of concentration, where the indicator is associated with the intensity values of the profile.

An indication of a concentration of a protein in a sample is obtained, for example, by comparing the most intense ion between profiles, or a designated precursor and/or product ion, or designated sets of precursor and/or product ions. Comparisons of concentrations are made, for example, by taking the averages or median values of intensities of precursors and products, and then taking the ratios of such averages or median values between proteins in different samples.

Optionally averages or median values of ratios of intensities are formed. Optionally, weighted or unweighted least-squares fitting is used to scale intensities of one set of ions to match another; the scaling factor obtained by least-squares fitting is used as an indication of concentration, or relative concentration of the proteins.

Next referring to FIG. 4, FIG. 5, FIG. 6, and FIG. 7, examples of some forms of protein profiles are described.

Figure 4:
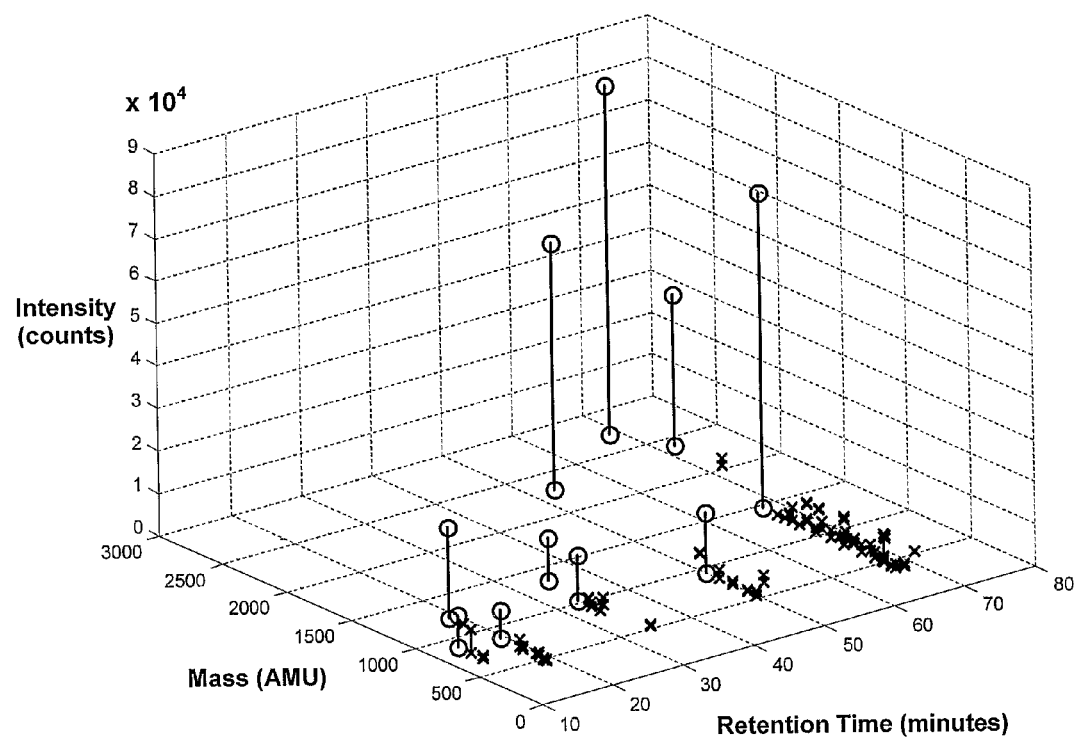
FIG. 4 is a three-dimensional graphical diagram of an example profile obtained from a sample transalodase, in accordance with one embodiment of the invention.

FIG. 4 is a three-dimensional graphical diagram of an example profile obtained from a sample of the protein transalodase (an enzyme) obtained from *E. Coli*, according to one embodiment. The profile includes data for precursor and product ions; the data are depicted in the graph as lines for each ion, located according to mass and retention time of the ion. The height of each bar corresponds to the intensity (ion count) of the associated ion. Precursor ions are identified by O's at the both ends of a line and product ions are identified by X's at both ends of a line. The profile includes data for ten precursor ions and for more than thirty product ions (not all of which are discernible in the diagram due to similar mass, time, and intensity values.)

Figure 5:
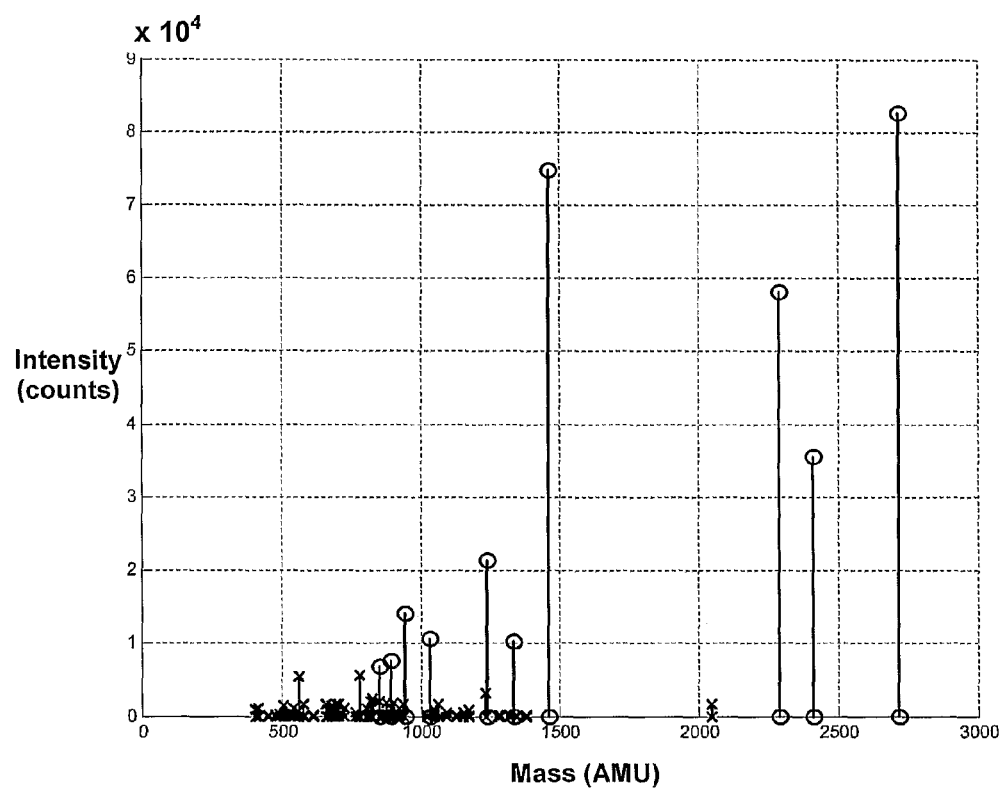
FIG. 5 is a two-dimensional bar graph of the profile of FIG. 4, showing intensity of precursor ions and product ions as a function of ion mass.

FIG. 5 is a two-dimensional bar graph of the profile of FIG. 4, showing intensity of precursor ions and product ions as a function of ion mass. As expected, the precursor ions generally have greater masses and intensities than the product ions since the product ions are fragments of precursors and more numerous.

Figure 6:
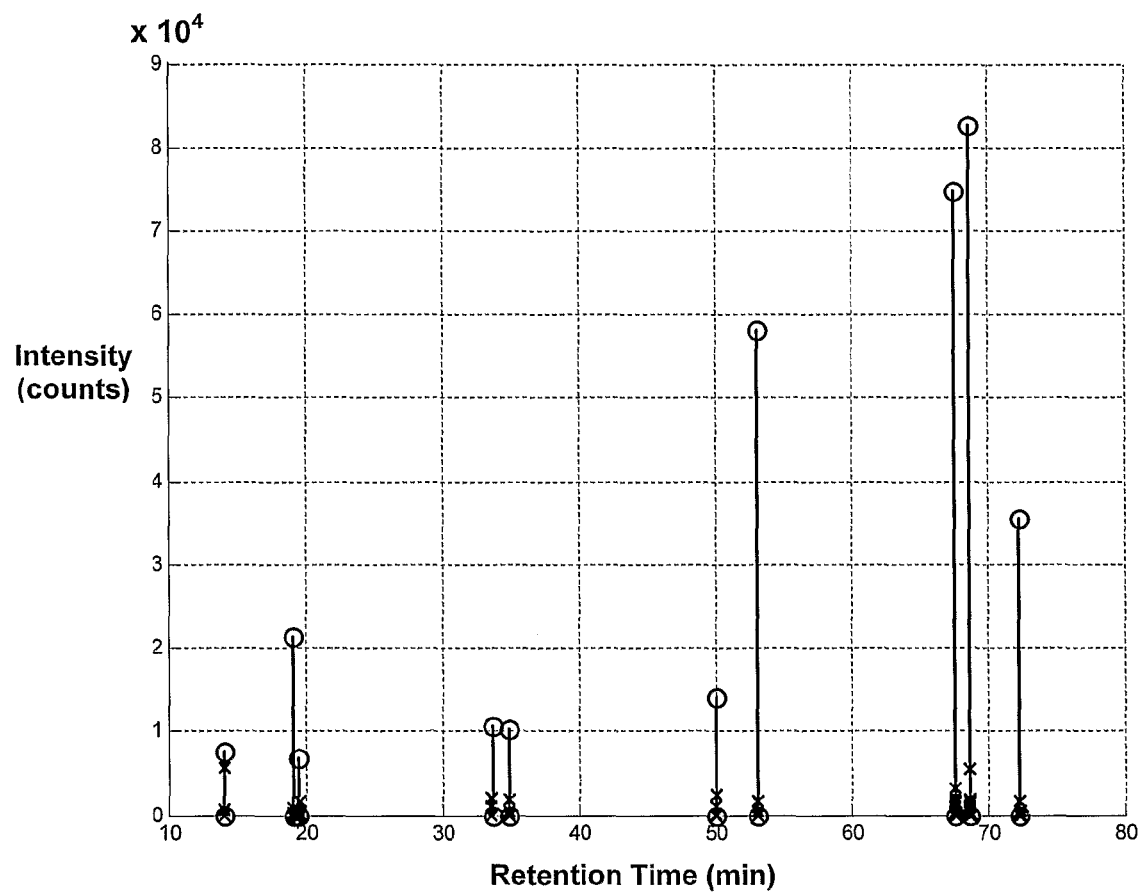
FIG. 6 is a two-dimensional bar graph of the profile of FIG. 4, showing intensity of precursor ions and product ions as a function of retention-time.

FIG. 6 is a two-dimensional bar graph of the profile of FIG. 4, showing intensity of precursor ions and product ions as a function of retention-time. The association between individual precursor ions and their product ions (i.e., same retention times) are observed.

Figure 7:
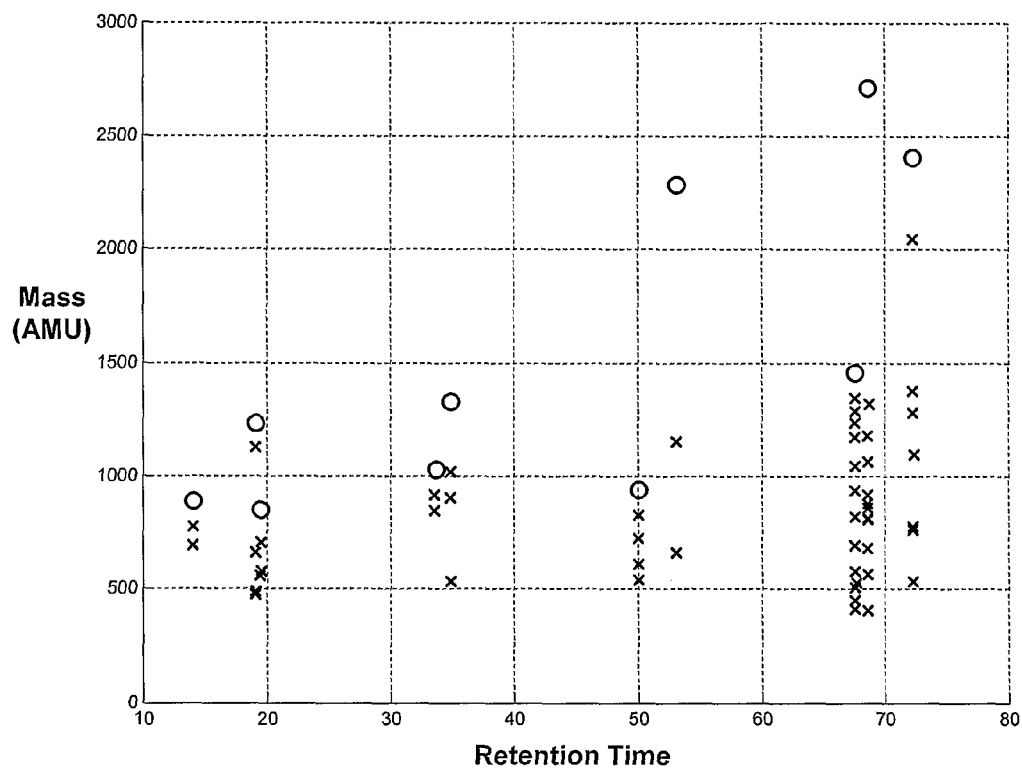
FIG. 7 is a two-dimensional plot corresponding to a top-down view of the profile of FIG. 4.

FIG. 7 is a two-dimensional plot corresponding to a top-down view of the profile of FIG. 4. The plot shows the location in mass and retention time of each precursor ion and product ion of the profile. Again, the association between individual precursor ions and their product ions are observed due to their alignment along a common retention time.

Figure 8:
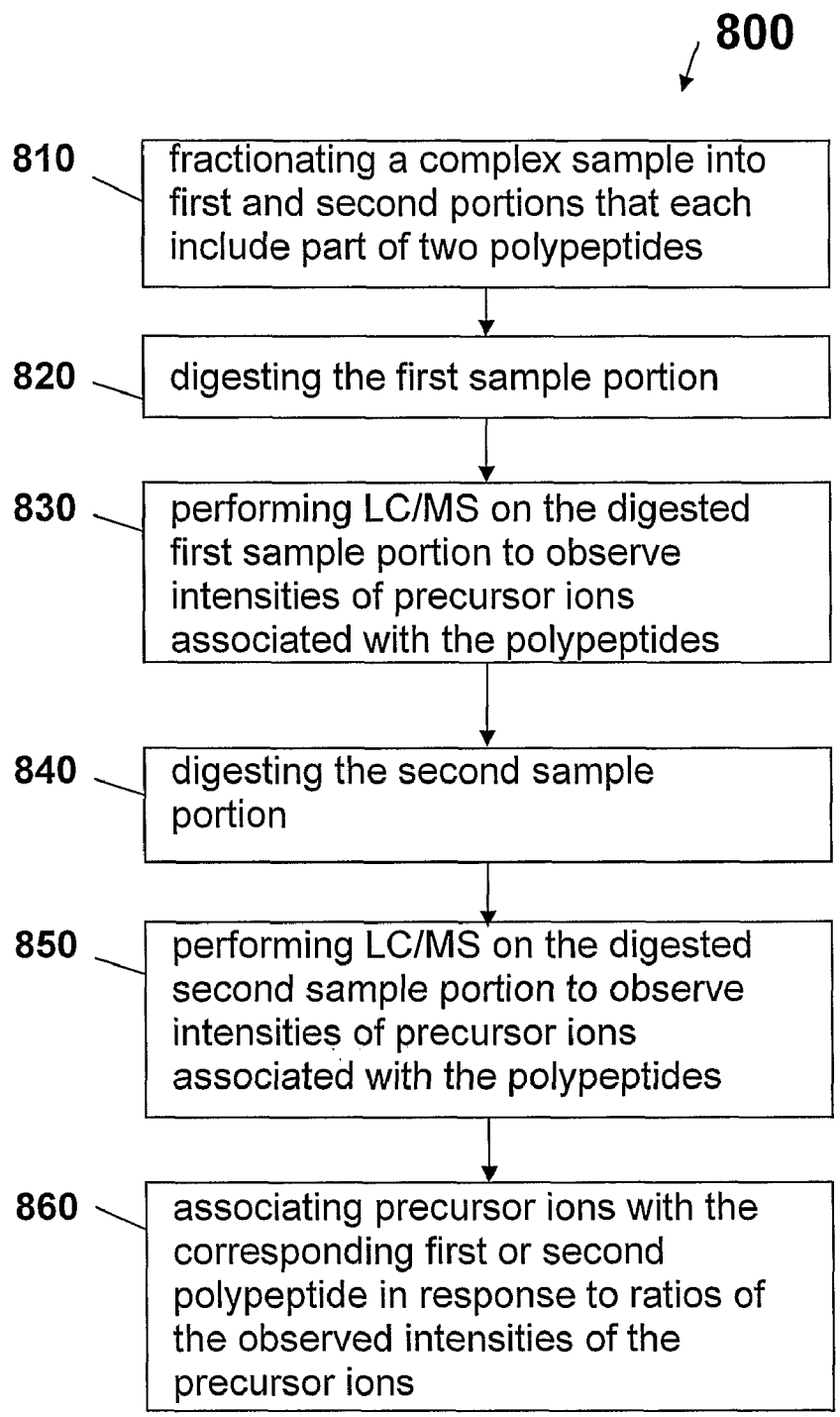
FIG. 8 is a flow diagram of a method for chemical analyses, in accordance with one embodiment of the invention.

Next referring to FIG. 8, some embodiments of the invention assist analysis of relatively complex samples, such as those that have multiple proteins, which may have precursors with overlapping chromatographic peaks. Some embodiments utilize sample fractionation to simplify and/or concentrate components of a complex sample and/or provide multiple sample portions for analysis and comparison.

In some embodiments, a sample is fractionated to increase the concentration of a protein in a fraction of the original sample. The concentrated sample is then optionally subjected to the above-described analysis methods 100, 200. Such embodiments increase the dynamic range of protein concentrations to which the methods 100, 200 are advantageously applied.

For example, utilizing some methods of the invention, all proteins present in a cell's proteome or a serum proteome are potentially observable for definition of protein profiles and/or identification of the proteins.

In some other embodiments, one of which is described with reference to FIG. 8, overlapping protein or precursor peaks are divided into two or more portions; data obtained from the portions is compared to assist a determination of which precursors are associated with the same protein. For example, after fractionation, the fractions are digested and separated via a chromatographic process. Separated precursors whose peak intensities from fraction to fraction correspond to protein concentration from fraction to fraction are then associated with the protein from which they arose.

By fractionating overlapping peaks of two polypeptides, one obtains a systematic change in ratio of subsequently produced precursors of the two polypeptides. LC/MS analysis of the fractions, such as by above-described methods that preserve retention-time information, produce precursor ion data. Fraction-related data may then be compared to determine which precursors are associated with a common polypeptide (in response to the different concentration ratio of the two polypeptides in each fraction.) Thus, if retention-time data is insufficient to determine the association, the additional information provided by fractionation often permits completion of the association process.

Alternatively, for example, a digested complex protein sample is subjected to a chromatographic separation process; sample portions are collected over a collection-time window that is preferably less than the full width of a chromatographic peak. Such a window ensures that at least two fractions will each include portions of a protein.

FIG. 8 is a flow diagram of a method 800 for chemical analysis, according to one embodiment of the invention. The method 800 includes fractionating 810 a complex sample having at least two polypeptides, digesting 820 and performing 830 LC/MS on the first sample portion, digesting 840 and performing 850 LC/MS on the second sample portion, and associating 860 precursor ions with their corresponding one of the first and second polypeptides in response to ratios of the observed intensities of the precursor ions in the first and second sample portions.

The complex sample is fractionated 810 into a least a first sample portion and a second sample portion that each include portions of the two polypeptides though in different concentration ratios. The fractions are digested 820, 840 via any suitable technique, such as those described above. LC/MS is performed 830, 850 to observe intensities of precursor ions associated with the polypeptides in the sample portions. Intensity related data then supports the determination of the association 860 of precursor ions with their polypeptide.

The method 800 is suited, in particular, to deconvolution of proteins that physically overlap during separation prior to fractionation 810. The method 800 is potentially most helpful in the case of two or more polypeptides exhibiting overlapping peaks that have indistinguishable retention times. The method 800 may thus be utilized, for example, in combination with a method such as the above described methods 100, 200 to generate a catalog of reliable profiles of proteins.

Any suitable fraction technique is used, including known techniques such as gel-permeation chromatography, size-exclusion chromatography, ion-exchange chromatography, and reverse-phase chromatography. Some suitable techniques utilize column overloading, pH gradients, and/or denaturing mobile phases.

The fractions are optionally collected in, for example, a series of vials. Alternatively, for example, each fraction is briefly held prior to subsequent analysis via, for example, a method such as the above-described methods 100, 200.

Fractionation 810 is preferably performed by oversampling, that is, by employing a fraction collection time of less than a peak width when collecting fractions of overlapping peaks. For example, if a peak width is 1 minute, a collection time of less than 1 minute is desirable.

Any suitable collection time value is selected. For example, one suitable collection time value is about a full-width at half maximum (FWHM) of a peak. Such a collection time assures that at least two fractions will include portions of at least two overlapping peaks. In some embodiments, three fractions are collected of overlapping peaks to provide sufficient confidence in the subsequent association of precursors with sample polypeptides. More generally, a greater number of narrower collection windows are optionally used to provide a simpler sample composition in each collected fraction.

Thus, a collection-window width is selected in any suitable manner. A width is optionally selected in response to an interactive process, in which a width that optimally assists deconvolution of peaks is determined. A single protein is optionally analyzed to empirically determine a peak width. Some fraction of the determined peak width is then selected for fraction collection, such as the FWHM of the determined peak. Alternatively, a peak width is determined theoretically.

In some alternative embodiments, proteins in a complex sample are concentrated via fractionation; the fractions are subsequently digested, and the digested fractions themselves are fractionated via a peptide fractionation protocol. For example, the fractionated peptides, at possibly a high column load, are fractionated by any one of a number of well-established protein fractionation techniques, such as gel-permeation chromatography, or reversed-phase chromatography, or ion exchange chromatography.

Each peptide fraction now represents a portion of the original peptide digest. This fraction is optionally concentrated and injected on a chromatographic column at a maximum column load. An LC/MS method used for all peptide digests is preferably the same (fractionated and unfractionated.) Thus, a given peptide will elute at the substantially the same retention time whether it is from the fractionated or unfractionated sample.

The fractionated peptides are then identified, for example, as described above. Any peptide seen in a fraction is seen at higher mass load with higher intensity, and more of its fragment ions will be seen above the detection limit of the instrument. Thus any high-energy validated peptide seen in the unfractionated digest will be seen in the fractionated digest with more ions, providing more sequence coverage. Peptides will also be seen in the fractionated digest with high-energy validation that were not seen in the unfractionated digest.

Retention time and accurate mass matching may be used to tie observed peptides in the fractionated and unfractionated samples together. Of particular use is the ratio of intensity of a peptide precursor seen in the fractionated sample to the precursor's intensity seen in the unfractionated digest. This ratio can be applied to all fragment ions seen in the fractionated digest, and thus one can infer the intensity of fragments as they would appear in the unfractionated digest. Thus one critical feature of some alternative profiles, the measurement of relative intensities of peptide precursors to a protein is preserved.

Figure 9A:
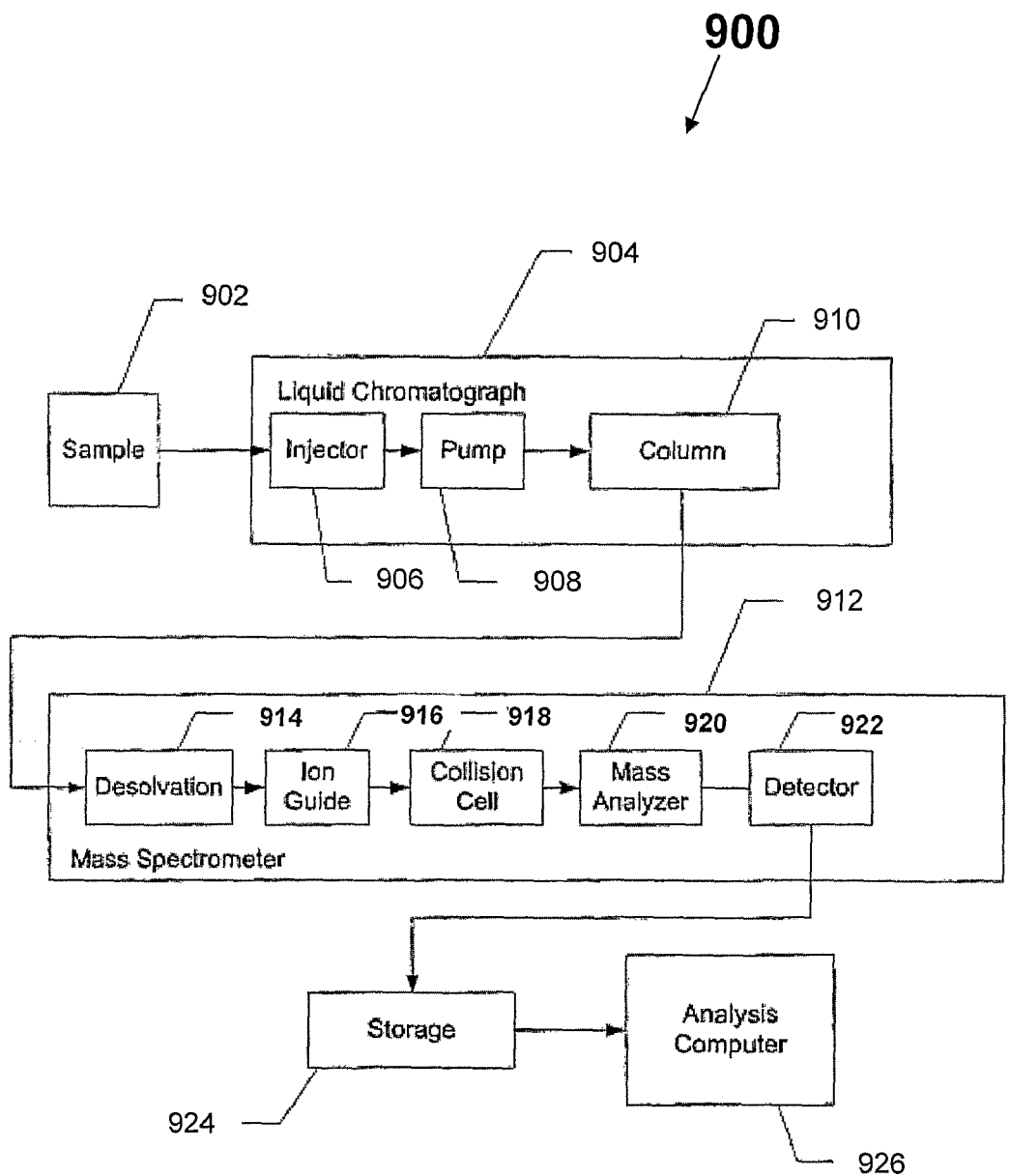
FIG. 9A is a block diagram of an LC/MS system, in accordance with one embodiment of the invention.
Figure 9B:
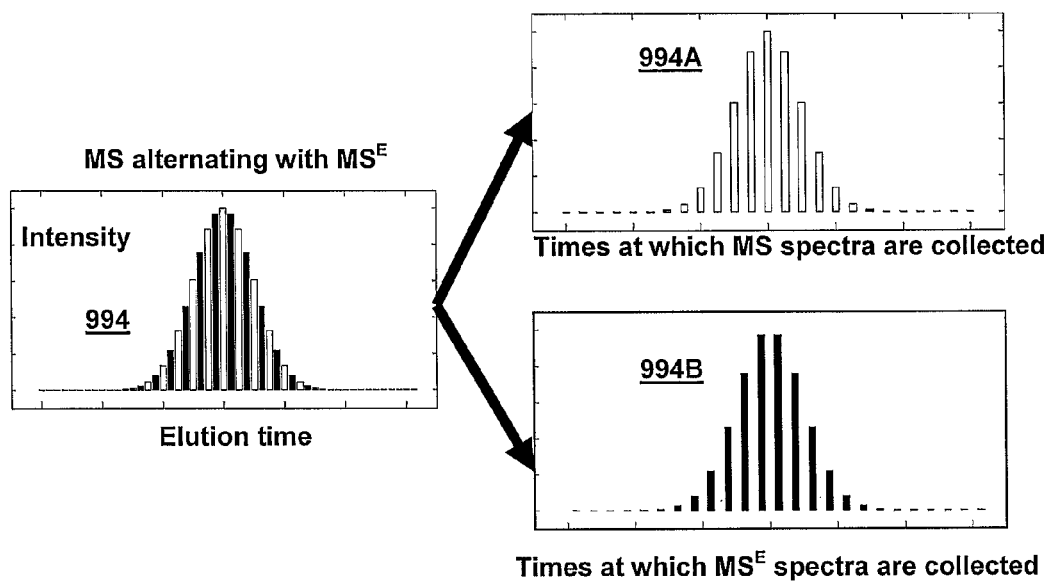
FIG. 9B shows three related graphs, which illustrate the collection of mass spectra in accordance with one embodiment of the invention.

Referring next to FIGS. 9A and 9B, some embodiments of the invention relate to LC/MS instruments. FIG. 9A is a block diagram of an LC/MS system 900, according to one embodiment of the present invention. The instrument includes a chromatography module 904 and a mass-spectrometer module 912 that receives an eluent from the chromatography module 904. The LC module 904 includes an injector 106 that receives a sample 902, a pump 908 and a column 910. the MS module 912 includes a desolvation/ionization device 914, an ion guide 916, a mass analyzer 920, and a detector 922. The system 900 also includes a data storage unit 924 and a computer module 926.

In operation, the sample 902 is injected into the LC module 904 via the injector 906. The pump 908 pumps the sample through the column 910 to separate the mixture into component parts according to retention time through the column 910.

The output from the column 910 is input to a mass spectrometer 912 for analysis. Initially, the sample is desolvated and ionized by the desolvation/ionization device 914. Any desolvation technique can be employed, including, for example, a heater, a gas, and a heater in combination with a gas or other desolvation technique. Ionization can be by any suitable ionization technique, including for example, electrospray ionization (ESI), atmospheric pressure chemical ionization (APCI), or other ionization technique. Ions resulting from the ionization are fed to a collision cell 918 by the ion guide 916.

The collision cell 918 is used to fragment the ions. In preferred embodiments, the collision cell 918 is operated in a switching mode to support observation of both precursor ions and product ions of the same eluting precursor material.

Any suitable switching techniques may be used, including known techniques. Some embodiments of the invention preferably use a fragmentation protocol in which a relatively simple alternating voltage cycle is applied to the cell 918. This switching is done at a high enough frequency so that multiple high- and multiple low-energy spectra are contained within a single chromatographic peak. Unlike some other switching protocols, the cycle is independent of the content of the data.

For example, as described in the '130 Patent, an alternating voltage is applied to the collision cell 918 to cause fragmentation. Spectra are collected for the precursors (no collisions) and fragments (results of collisions.)

Alternative embodiments utilize other means for fragmentation, such as any suitable collision fragmentation or reaction device, including any suitable known device. Some optional devices include: (i) a Surface Induced Dissociation ("SID") fragmentation device; (ii) an Electron Transfer Dissociation fragmentation device; (iii) an Electron Capture Dissociation fragmentation device; (iv) an Electron Collision or Impact Dissociation fragmentation device; (v) a Photo Induced Dissociation ("PID") fragmentation device; (vi) a Laser Induced Dissociation fragmentation device; (vii) an infrared radiation induced dissociation device; (viii) an ultraviolet radiation induced dissociation device; (ix) a nozzle-skimmer interface fragmentation device; (x) an in-source fragmentation device; (xi) an ion-source Collision Induced Dissociation fragmentation device; (xii) a thermal or temperature source fragmentation device; (xiii) an electric field induced fragmentation device; (xiv) a magnetic field induced fragmentation device; (xv) an enzyme digestion or enzyme degradation fragmentation device; (xvi) an ion-ion reaction fragmentation device; (xvii) an ion-molecule reaction fragmentation device; (xviii) an ion-atom reaction fragmentation device; (xix) an ion-metastable ion reaction fragmentation device; (xx) an ion-metastable molecule reaction fragmentation device; (xxi) an ion-metastable atom reaction fragmentation device; (xxii) an ion-ion reaction device for reacting ions to form adduct or product ions; (xxiii) an ion-molecule reaction device for reacting ions to form adduct or product ions; (xxiv) an ion-atom reaction device for reacting ions to form adduct or product ions; (xxv) an ion-metastable ion reaction device for reacting ions to form adduct or product ions; (xxvi) an ion-metastable molecule reaction device for reacting ions to form adduct or product ions; and (xxvii) an ion-metastable atom reaction device for reacting ions to form adduct or product ions.

The output of the collision cell 918 is input to a mass analyzer 920. The mass analyzer 920 is any suitable mass analyzer, including quadrupole, time-of-flight (TOF), ion trap, magnetic sector mass analyzers as well as combinations thereof. The detector 922 detects ions emanating from the mass analyzer 920. The detector 922 is optionally integral with mass analyzer 920. For example, in the case of a TOF mass analyzer, the detector 922 is optionally a microchannel plate detector that counts intensity of ions, i.e., counts numbers of impinging ions. The storage medium 924 provides permanent storage for storing the ion counts for analysis. For example, storage medium 924 is an internal or external computer disk. The analysis computer 926 analyzes the stored data. Data can also be analyzed in real time without requiring storage in a storage medium 924. In that case, the detector 922 passes data to be analyzed directly to computer 926 without first storing it to permanent storage.

The collision cell 918 performs fragmentation of the precursor ions. Fragmentation can be used to determine the sequence of a peptide and subsequently lead to the identity of the originating protein.

The collision cell 918 utilizes a gas, such as nitrogen. When a charged peptide interacts with the gas' atoms, the resulting collisions can fragment the peptide by breaking it up at one or more characteristic bonds. The most common resulting fragments are described as Y- or B-ions. Such fragmentation can be accomplished as on-line fragmentation by switching the voltage in a collision cell between a low voltage state (low energy) which obtains MS spectra of the peptide precursor, with a high voltage state (high energy) which obtains MS spectra of the collisionally induced fragments of the precursors. High and low voltage are referred to as high and low energy, since a voltage is used to impart kinetic energy to an ion.

The chromatographic module 904 includes any suitable chromatography instrument(s), including known instruments, such as column-based instruments. Suitable columns include columns known to one having ordinary skill in the chromatographic arts. The column can be formed from, for example, metallic or insulating materials. Suitable materials include known materials such as steel, fused silica, or lined materials. The column can include more than one column, disposed in serial and/or parallel configurations. For example, the column can be a capillary column and can include multiple capillary tubes.

The computer module 926 is in data communication with other components of the system 400 via wired and/or wireless means, such as those known in the data-communication arts. The module 926 receives process data, for example, from the mass-spectrometer module 912, and provides control signals. The module 926 is optionally configured to implement methods described herein, such as the methods 100, 200 for chemical analysis described above. The module 926, in various illustrative embodiments, is implemented in software, firmware, and/or hardware (e.g., as an application-specific integrated circuit), and includes, if desired, a user interface. The module 926 includes and/or is in communication with storage component(s), such as the storage unit 924.

Suitable implantations of the module 926 include, for example, one or more integrated circuits, such as microprocessors. A single integrated circuit or microprocessor in some alternative embodiments includes the module 926 and other electronic portions of the system 900. In some embodiments, one or more microprocessors implement software that enables the functions of the module 926. In some embodiments, the software is designed to run on general-purpose equipment and/or specialized processors dedicated to the functionality herein described.

An LC/MS experiment can produce as one of its outputs a mass chromatogram. A mass chromatogram is a set or group of responses (intensities) recorded as a function of time at a specific mass value. In a mass chromatogram, the mass value may be the central value within a range. That is, the intensity at a given time may be obtained by combining intensities collected over a specified range of mass values. Typically, a mass chromatogram contains one or more chromatographic peaks.

A single molecule, or chemical entity, has a specific mass. In an LC/MS experiment the ionized form of that molecule is observed as a chromatographic peak at the mass value of that ion divided by its charge (mass-to-charge ratio). A chromatographic peak has a peak profile, or elution profile. The chromatographic peak profile can be characterized using several features, including an apex retention time, a peak width, a lift off time and a touch down time. A chromatographic peak width can be described as a width at a specific peak height (FWHM, width at 50% height), or a width between inflection points, or as a standard deviation. The apex intensity or chromatographic peak height is the maximum intensity found in a chromatographic peak profile. Generally, the apex intensity is baseline corrected.

A molecule in an eluent that is separated by a chromatographic separation, and elutes from the column is referred to as the common eluting molecule or originating molecule. The originating molecule is ionized through the ionization source of the mass spectrometer. The resulting ions are measured in an LC/MS or LC/MS$^E$. As a result of isotopic composition and or fragmentation processes, each originating molecule can give rise to multiple categories of ions, each having a unique value of mass and charge. The ion corresponding to the originating molecule is termed the precursor ion, or just the precursor.

In peptide digests the originating molecule is a peptide and the ion corresponding to the peptide is referred to as the precursor. Any ion derived from the originating molecule, whether the processor or a fragment, must have the same retention time and chromatographic peak profile as the precursor.

In an LC/MS experiment an ion can be described and/or referred to by its retention time, mass-to-charge ratio, and intensity. A single molecule can appear in an LC/MS chromatogram as a cluster of ions. A peptide gives rise to one or more ion clusters. Each cluster corresponds to a different charge state (e.g., Z=1 or Z=2). Each ion in a cluster corresponds to a different isotopic composition of the peptide. In a cluster of ions from a common peptide, the monoisotope is the ion having the lowest mass, where all the isotopes are in their most abundant, low mass state. Since the ions in the cluster come from a common originating molecule, they must share a common retention time and peak profile.

An originating molecule can give rise to multiple ions due to isotope and charge effects. Additional, important sources of ions are fragments of the originating molecule. These fragments arise from processes that break up the originating molecule. These processes can occur in the ionization source or in a collision cell. Because fragment ions derive from a common eluting, originating molecule, they must have the same chromatographic retention time and peak profile as the originating molecule.

Generally, if an originating molecule gives rise to N ions, and if these are adequately resolved by the mass spectrometer, then there can be N mass chromatograms, where each mass chromatogram contains a peak, a chromatographic profile of an ion that derives from the originating molecule. The retention time and peak profile of each of these N ions will be identical. The term common-retention-time-entity refers to all ions of an originating molecule that, in an LC/MS separation, give rise to chromatographic peaks all having the same retention times and peak shapes.

The retention time and peak shapes of ions that derive from a common originating molecule are the same because the time of ion formation, fragmentation, and ion detection is generally much shorter then the peak width of the originating molecule. For example, a typical chromatographic peak width, measured at full-width at half-maximum (FWHM) is 5 to 30 seconds. The time of ion formation, fragmentation, and detection is typically sub milliseconds. Thus on a chromatographic time scale, the time of ion formation is an instantaneous process. It follows that differences in observed retention times of the ions that derived from an originating molecule is effectively zero. That is, sub-millisecond retention time differences between ions that derived from an originating molecule are small compared to the chromatographic peak width.

The ions that are associated with an originating molecule fall into one of several categories. An ion derived from an originating molecule can be a precursor, a fragment of the precursor, or a fragment of a fragment, or a neutral loss of any of the above masses. Any of these masses can be seen in one or more discrete isotopic states, and in one or more charge states.

In the case of peptides, a given peptide is generally seen to be a cluster of ions, each in a distinct isotopic state, and each in one or more charge states. Ideally the ionization source produces precursors that are a protenated form of the neutral originating molecule. One or more protons can be attached to the neutral molecule and thus the precursors can be one or more mass units higher than the neutral with charge Z=+1, or +2, etc. In practice, this precursor (termed mwHPlus) may be accompanied by lower mass entities that result from the loss of neutral molecules such as water, ammonia, or phosphate. Fragmentation can occur in the source, yielding, typically, Y- or B-ions. Fragmentation can be also be deliberately induced by down-stream interactions with gas molecules in a collision cell.

With respect to ions that are generated from collision-induced disassociation of intact precursor ions, the fragment product ions associated with their parent precursor ion. This association is accomplished without requiring the instrument to pre-select a single precursor for subsequent fragmentation using the mass spectrometer in a High-Low Data Acquisition Mode. More specifically, associated ions are appropriately grouped when multiple precursors are fragmenting simultaneously, at essentially the same retention time. Thus, embodiments of the present invention can assign product ions to their respective precursor when there is more than one precursor fragmenting at the same moment in time. Moreover, embodiments of the present invention can significantly reduce the computational burden for de-isotoping and charge-state reducing ions to their common, singly charged annotation (i.e. MH+).

The method of the current invention can be applied to mixtures other than that of peptides, provided originating molecules give rise to precursor ions and fragment ions. Thus embodiments of the present invention can be used in proteomics, metabolomics, and metabonomics.

The retention time and chromatographic peak profile of a molecule (peptide, metabolite, natural product) eluting from a chromatographic support matrix, such as column 910, is a function of the physical interaction of that molecule between the support matrix and mobile phase. The degree of interaction that a molecule has between the support matrix and the mobile phase dictates the chromatographic profile and retention time for that molecule. In a complex mixture, each molecule is chemically different. As a result, each molecule can have a different affinity for the chromatographic matrix and the mobile phase. Consequently, each can exhibit a unique chromatographic profile.

Generally, a chromatographic profile for a specific molecule is unique and describes the physicochemical properties of that molecule. Parameters optionally used to characterize the chromatographic peak profile of a given molecule include the time of initial detection (liftoff), normalized slope, the time of inflection points relative to the time of the peak apex, the time of maximum response (peak apex), the peak width, at inflection points, at full-width-at-half-maximum (FWHM), peak shape asymmetry, and the time of the final detection (touch down) to name only a few.

FIG. 9B shows three related graphs that illustrate the collection of mass spectra during a period of time that covers an eluted peak of a precursor, according to one embodiment of the invention. A first graph 994 illustrates the alternating collection over elution time of low-energy spectra (i.e., spectra from unfragmented precursors, labeled "MS") and high-energy spectra (i.e., spectra from fragmented precursors, that is, product ions, labeled "$MS^E$".) Second and third graphs 994A, 994B respectively illustrate the MS and $MS^E$ spectral collection times and the reconstruction of the retention time peak associated with the precursor.

The reconstructed peak represents the chromatographic elution profile of a single precursor. The horizontal axis corresponds to elution time of the peak profile. The vertical axis corresponds to arbitrary units of intensity associated with the time-varying concentration of the precursor as it elutes from the chromatographic column.

An eluting precursor, passed to the mass spectrometer, thus produces ions in both low- and high-energy modes. The ions produced in the low-energy mode are primarily those of the precursor ions in possibly different isotopic and charge states. In proteomic studies, the precursor ions are peptides generated from enzymatic digestion (typically a tryptic digest) of the intact protein(s). In high-energy mode, the ions are primarily different isotopes and charge states of the fragment ions of those precursors. High-energy mode can also be referred to as elevated-energy mode.

In the graph 994, the alternating white and black bars thus represent the times at which spectra are collected with low and high-energy voltages of the eluting chromatographic peak. The low-energy graph 994A depicts the times at which a low-energy voltage is applied in the collision cell 918, resulting in low-energy spectra. The high-energy graph 994B depicts the times at which a high-energy voltage is applied in the collision cell 918, resulting in high-energy spectra.

The chromatographic peak of the precursor is thus sampled multiple times, by the high- and low-energy modes. From these multiple samples, accurate retention times of all the ions associated with the peak and seen in the high- and low-energy spectra can be inferred. These accurate retention times are obtained by interpolation of the intensities sampled by the respective spectra.

What will now be described are techniques that may be used in connection with performing retention time matching of precursors and related product ions included in an input data set.

In connection with a sample or mixture, such as a complex protein sample including multiple proteins, many precursor ions may have a same retention time. When a precursor ion is fragmented, the product ions produced as a result of the fragmentation will also have the same retention time as that precursor. Due to the large number of precursor ions that may have the same retention time, product ions from different precursors may have substantially the same retention time. As a result, it may be difficult to match product ions to the respective, correct precursor ions. The matching of product ions to the appropriate precursor ion from which the product ions are generated has many applications as described herein and known to those skilled in the art.

In the context of LC/MS, the retention time matching technique finds those product ions and the related precursor ion from which the product ions are derived having the same retention time and peak shape. The techniques described herein provide for association of product ions with precursors ensuring that product ions and precursors having substantially the same measured retention time are included in the output spectrum based upon retention time alignment.

The techniques for performing retention time matching may be used in connection with complex samples as well as simple samples. Complex samples may include, for example, a protein mixture as well as any one of a variety of different biological samples known in the art such as a serum, tissue, and cells. The retention time matching techniques may also be used in connection with a simple sample of a single polypeptide.

The techniques for retention time matching of precursors to related product ions may be used, for example, in connection with the techniques described herein to produce a polypeptide profile used in protein identification techniques. In connection with such a profile for a protein as described herein, a set of precursor ions determined as the most intense precursors for the protein may be used to identify the protein. The profile may be used to detect, identify, track and/or quantify the protein to a sufficient specificity so that the protein may be distinguished from other proteins. The profile may also include additional information regarding each of the most intense precursors. The additional information may include, for example, one of more product ions associated with each of the precursors, data (e.g., such as retention time, intensity and/or mass or m/z) about each of the one or more product ions. The retention time matching techniques may be used to identify the product ions associated with the most intense precursors as included in the profile. Information from the profile, such as the mass of the most intense precursor ions along with the masses of a sufficient number of its product ions, can identify the sequence of the protein to a high degree of confidence.

The retention time matching techniques described in following paragraphs may be used to detect, identify, track and/or quantify peptides and proteins and addressing problems in proteomics. The retention time matching techniques described herein may also be used in connection with samples or mixtures that may be characterized as other than biological. In connection with proteomic applications, the peptides may result from enzymatic digestion of sample proteins. Reliable identification of peptide precursors allows identification and quantitation of sample proteins.

The retention time matching techniques described herein may be used to reliably assign or match product ions to precursors in a deterministic manner without utilizing other methodologies, such as statistical methods, to compensate for incorrect matching of product ions and precursors. The precursors and related product ions identified using the techniques herein may be stored in a database alone, or in connection with other data such as when annotating an existing data store.

Although reference in illustrative examples herein may be made to applications using protein digests analyzed using the foregoing technique described in Bateman, an embodiment may produce data sets using other methodologies known in the art such as, for example, data dependent analysis (DDA) used to isolate selected precursor ions and identify product ions for the selected isolated precursor. In one embodiment, a mass spectrometer may be used to perform DDA in which the mass spectrometer includes a collision cell and a quadrupole. When operating in accordance with the DDA technique, the quadrupole is used as a filter in a first phase to selectively isolate and select only precursors of interest. Thus, only selected precursors are produced as an output of the first filtering phase. The selected precursors are then passed to a collision cell where they are fragmented, as using a sufficiently high voltage, to generate fragments or product ions and obtain a desired number of scans for the isolated precursor and product ions. The foregoing DDA technique may be repeated for isolating different precursors and obtaining a desired number of scans for the precursors and related product ions.

An embodiment may determine masses of particular precursors of interest using a variety of different techniques. For example, in one embodiment utilizing the Bateman techniques as described elsewhere herein, the low energy (LE) cycle or mode may be used to generate spectra including one or more precursor ions. Other techniques used to generate the input data set, such as the DDA technique, may also be used to isolate precursors and determine their particular masses. The selected precursors and associated masses may be subsequently identified in the input data set.

In one embodiment using the techniques herein, mass spectra as produced from different experiments using a mass spectrometer may be compared. The retention time matching techniques described herein may include the mass spectra in an input data set, and may combine the foregoing mass spectra by determining an intersection of the mass spectra. For simplicity of illustration and explanation, the mass spectra may include data related to a single precursor and product ions having substantially the same measured retention time and peak shape as the precursor. However, the product ions have different mass or m/z values. The retention time of the single precursor and its related product ions in each of the different spectra may be within an expected retention time window of error incurred due to possible measurement error. In one embodiment, the window of error may be within a threshold of $1/10^{th}$ of a peak width of the retention time of the precursor as determined using the full width half maximum (FWHM) methodology. As known in the art, FWHM is determined as the distance between two points on either side of the mass spectral peak at which the curve reaches half its maximum value. An embodiment may also use other values as the foregoing window of expected error in accordance with the expected error of system and methodologies utilized in an embodiment.

The mass spectra included in the data set may include precursors having a retention time within the foregoing retention time window or window of error. Each of the mass spectra may then be aligned or normalized in accordance with a single retention time. For example, the mass spectra in the data set may include those mass spectra having a precursor with a retention time of "n" +/−$1/10^{th}$ the chromatographic FWHM of the mass spectral peak. Each of the spectrum in the data set may then be aligned at a single retention time, such as "n". In the alignment process, each precursor ion in a spectrum is shifted by a quantity and in a direction to align the precursor at a retention time of "n". Additionally, the product ions of the spectrum are also shifted by the same quantity and in the same direction in accordance with the shift of the precursor of the spectrum. The foregoing alignment is repeated for each of the spectrum After alignment, if a product ion falls within the foregoing window of error in each of the spectra in the data set, then that product ion is determined to also have the same retention time as the precursor and is matched with the precursor for which the alignment process is performed with the retention time of "n". In contrast, if the product ion is not within the foregoing window of error for each of the spectra, the product ion is determined to be not a match for the precursor. As such, the retention time matching of precursor and related product ions may be performed in a deterministic, reliable manner. The result may be in the form of an output spectrum containing the precursor and all identified product ions from the mass spectra of the input data set.

The data set may include spectra, such as MS spectra, generated using a variety of different techniques. For example, the spectra may be obtained using an LC/MS analysis of complex mixtures using the techniques of Bateman or the DDA technique. The data set may also be obtained from MALDI-MS-MS, and using spectrometers with high or low resolution.

The product ions as included in a data set for use in connection with the retention time matching techniques may be produced using a variety of different methodologies known in the art. The product ions may be produced using any one of a variety of different fragmentation techniques. An embodiment may use a mass spectrometric (MS) methodology as described in Bateman using a high- and low-energy switching protocol applied as part of an LC/MS analysis of a single injection of a peptide mixture. In such data the low-energy (LE) spectra contain ions primarily from unfragmented precursors, while the high-energy (HE) spectra contain ions primarily from fragmented precursors.

Each spectrum in the data set to which the retention time matching techniques described herein are applied may be obtained from an independent analysis or experiment. For example, in an LC/MS context, each of the M spectra included in an input data set may be obtained from M different injections. These M injections may be from M injections of the same aliquot (e.g., replicate injections). Alternatively, each of the M injections may use a different sample mixture. An embodiment may also utilize a data set in which the spectra are produced from some number of replicate injections of some number of different sample mixtures.

The retention matching technique depends on the principle that product ions maintain strict association with the precursor ion from which the product ions are derived. This association may manifest itself by both the product ions and the precursor ion appearing at substantially the same measured retention time. The retention matching technique takes advantage of the fact that ions which are unrelated to a selected precursor will not maintain the foregoing association for the spectra analyzed in the input data set.

The retention time matching technique makes use of the mathematical operation of Venn intersection as applied to masses of the ions. Two ions, such as a precursor and a product ion, are deemed to be related if their masses lie within a predetermined mass tolerance window and each have a same retention time as determined in accordance with the error window size or retention time window as described elsewhere herein. In an embodiment, the error window size or retention window used in connection with matching a precursor with a product ion, may be related to the chromatographic FWHM of the mass spectral peaks, or other tolerance as related to the resolution of the instrument, such as the MS instrument used to obtain the spectra in the input data set.

It should be noted that as described herein, two ions may be deemed to have a same mass if a first mass of the first ion is within a predetermined mass tolerance of a second mass of the second ion. This mass tolerance may be used in connection with the techniques described herein with respect to precursor ions as well as product ions. In one embodiment, the mass tolerance may be +/−$1/10^{th}$ of the FWHM of the peak as may be included in a mass spectrum expressed in parts-per-million (PPM). Other mass tolerances may be used in connection with, and may vary with, an embodiment.

As a result of using the retention time matching technique described herein, an output spectra may be produced which includes those product ions deemed to be related to a precursor ion.

The techniques for retention time matching using Venn intersection may be applied to M spectra such that a product ion is included in the output spectrum only if it appears in all M spectra within the predetermined window size. Alternatively, an embodiment may apply the retention time matching using the Venn intersection such that a product ion is included in the output spectrum if the product ion appears in a specified portion of the M spectra within the predetermined window size. The portion size selected may vary with an embodiment.

The retention time matching techniques described herein may be applied, for example, to spectra in which the number of unrelated ions greatly exceeds those product ions that are related to a given precursor. These techniques may be used to simplify the spectra that, taken individually, may be characterized as too complex to be interpreted using existing data interpretation techniques.

As one example, a spectrum may include 4 product ions that are derived from a common precursor peptide. The foregoing 4 product ions may be included in a spectrum also including 200 other product ions which are unrelated to the precursor peptide. The retention time matching techniques described herein may be applied to multiple spectra, including the foregoing four product ions and other unrelated product ions. Ions unrelated to the precursor will not be included in the output spectrum produced as a result of applying the retention time matching techniques. For example, the retention time matching techniques described herein may be used in connection with an input set including three spectra in which the foregoing 4 product ions related to the common precursor may be identified as such. The number of spectra needed for reliable matching may vary with precursor and other factors particular to an embodiment. Given the precursor mass and the four masses of the related product ions found in the simplified output spectrum produced as a result of the techniques herein, a search engine may be used in identifying a peptide. Such search engines may include, for example, MASCOT from Matrix Sciences. As another example, the techniques described herein may utilize an input data set including as few as two input spectra. Each of the input spectrum may include a precursor of interest and as few as a single product ion associated with the precursor of interest.

In the context of LC/MS, the retention time matching technique finds those product ions and the related precursor ion from which the product ions are derived having the same retention time and peak shape. The techniques described herein provide for association of product ions with precursors ensuring that product ions and precursors having substantially the same measured retention time are included in the output spectrum based upon retention time alignment.

In addition to spectra, an input data set used in connection with the techniques described herein may include ions in an ion list. An ion list may be obtained, for example, from three-dimensional data such as may be acquired utilizing LC/MS or other experimentation and processing methodologies. Each ion included in an ion list may be annotated by the ion's retention time, mass or m/z, and/or intensity. In such instances where three-dimensional data is utilized, spectra may be obtained, for example using retention time binning as described, for example, in Plumb et al., US Patent Publication No. 2005/0127287, filed on Nov. 16, 2004, titled Method of Using Data Binning in the Analysis of Chromatography/Spectrometry Data, which is incorporated by reference herein, or PCT Patent Application No. PCT US2005/004180, filed on Feb. 11, 2005, titled Apparatus and Method for Identifying Peaks in Liquid Chromatography/Mass Spectrometry Data and for Forming Spectra and Chromatograms, by Gorenstein et al.

The retention time matching techniques described for matching precursor and product ions using the Venn intersection may be applied to a variety of different areas and used in connection with a variety of different methodologies. For example, these techniques may be used in proteomics and small molecule studies. These techniques may be used to detect precursor and related product ions in replicate injections of a sample and the storage of such information in the database, such as an annotated peptide catalog and included in a peptide profile. Such stored information may be extracted from a data store for comparison against characteristics of unknown samples. Such stored information may be used to detect, identify, and/or quantify an unknown sample.

In connection with the techniques described herein, multiple precursors having a same retention time in one injection are found to have slightly different retention times and other injections even under replicate conditions, for example, as may be determined utilizing the Bateman technique. Accordingly, product ions associated with multiple precursors may have a single retention time in the first injection and the multiple precursors may have slightly but measurably different retention times in other injections. As a result, the product ions that may have a first retention time in a first injection may have a slightly different retention time in a subsequent injection even under replicate conditions. The techniques described herein advantageously utilize the fact that as long as the difference in measured retention time between the precursor and the product ions are within the specified retention time window of error or threshold for a specified number of experiments, then the product ions may be associated with the precursor. Furthermore, the techniques described herein, utilize the fact that unrelated product ions will not remain within the foregoing retention time window or threshold for the specified number of experiments. Thus, the foregoing techniques for retention time matching provide for separating product ions which are related from those which are unrelated with respect to a precursor.

It should be noted that the foregoing techniques compare mass values of spectral peaks within the input data set or spectrum. No prior knowledge regarding mass values or m/z values for the precursor and/or product ions is needed. Additionally, no prior knowledge of the sequence for a given protein is needed to utilize the techniques described herein on a sample although the techniques described herein may be used to further annotate a database or catalog.

The output produced as a result of the techniques described herein may be in the form of a spectrum. The spectrum may include the precursor and the one or more product ions included as a result of determining the Venn intersection. The resulting output spectrum may be stored, displayed, used in connection with searching to identify an unknown peptide, retention time tracked, used in connection with intensity ratios between different injections, and the like. In one embodiment, multiple output spectra may be determined for the same pairing of precursor and product ions. For example, a first experiment may determine a first output spectrum having a first intensity. A second experiment may be performed for the same sample having a different intensity under replicate conditions producing a second output spectrum. The output spectrum having the greater intensity may be stored.

Figure 10:
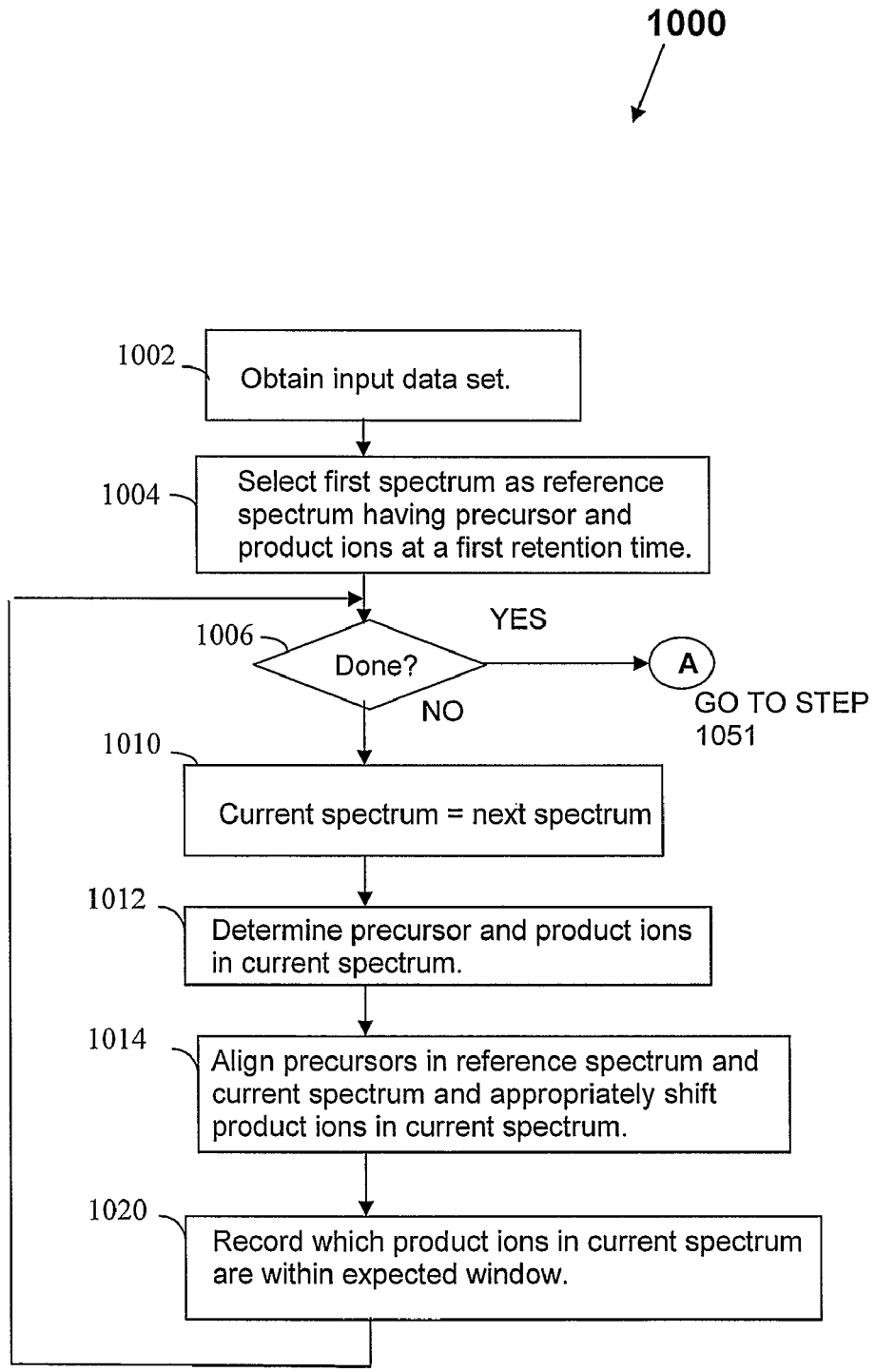
FIG. 10 and FIG. 11 are flow diagrams of processing steps that involve retention time matching of a precursor and its related product ions, in accordance with one embodiment of the invention.
Figure 11:
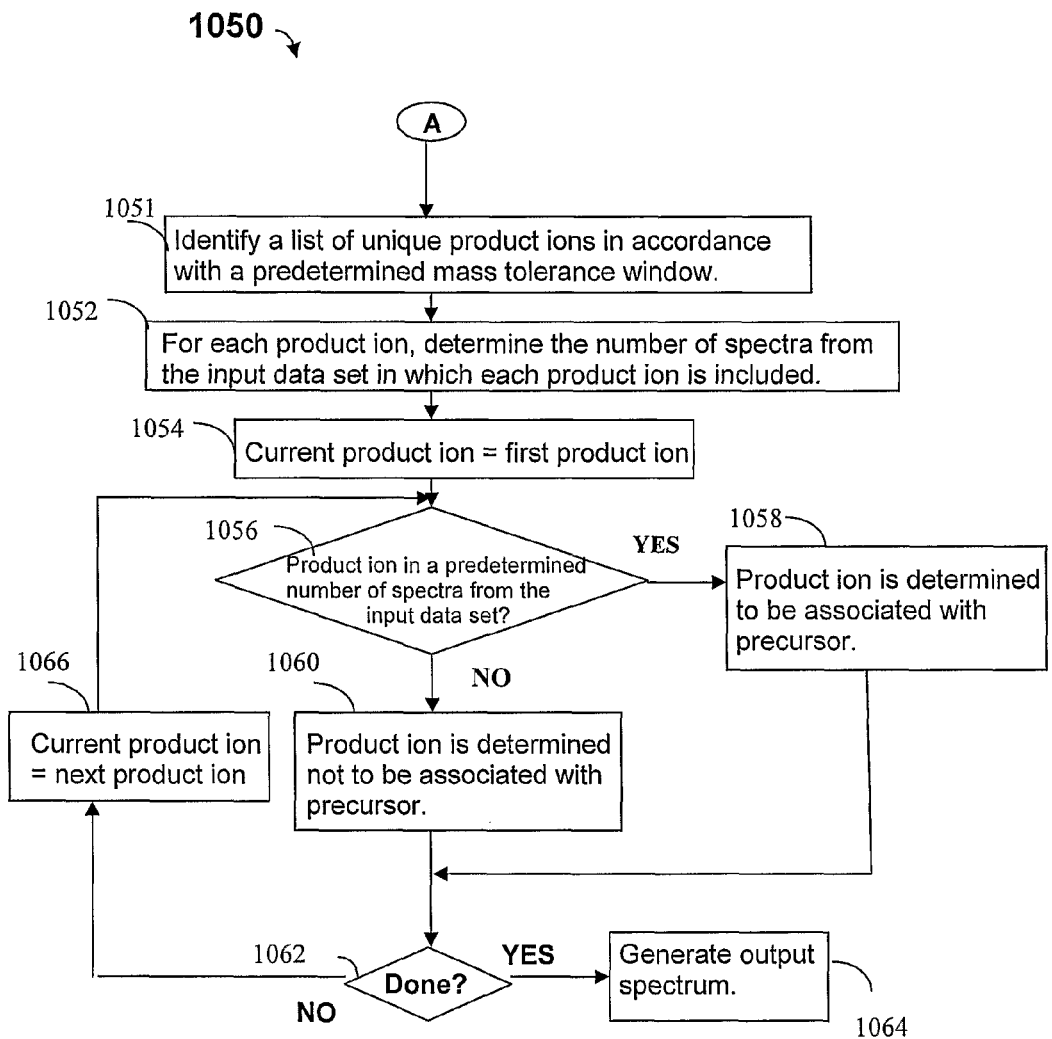

Referring now to FIG. 10 and FIG. 11, shown are flowcharts of processing steps that may be used in an embodiment in connection with performing retention time matching of a precursor and its related product ions. The steps of FIG. 10 and FIG. 11 summarize processing just described. At step 1002, an input data set is obtained. As described herein, the input data set may include data from multiple injections. The input data set may be in any one or more of a variety of different forms including ion lists and spectra although spectra are included in the steps of flowcharts 1000 and 1050 for illustration. At step 1004, a first spectrum of the input data set is selected. The first spectrum may be referred to as the reference spectrum. The injection which was used in obtaining the first spectrum may be referred to herein as the reference injection. A precursor for the reference spectrum is determined. In one embodiment, one or more precursors may be determined as those ions having the greatest mass and intensity. For purposes of illustration in connection with the flowcharts 1000 and 1050, it is assumed that only a single precursor is included in each spectrum of the input data set. As described herein, such as in connection with the Bateman technique, different methodologies may be utilized to determine the mass of a selected precursor of interest. With reference to the Bateman technique, masses of precursors may be determined by examining the resulting spectra produced using a LE scan.

In this first spectrum or reference spectrum, the product ions having the first retention time within the expected retention time error window or threshold may be characterized as product ion candidates for the precursor. After performing processing of the common retention time matching technique described herein, it is known which of the product ion candidates are matched or associated with the precursor ion.

When determining the product ions of the reference injection occurring at the same retention time as a precursor of the reference injection, all product ions occurring within the expected error window of the retention time are considered. For example, a precursor may have a retention time of T1 in the reference injection. A first product ion may have a retention time which falls within T1 and T1+/− the expected error window or retention time window. The first product ion is considered as a candidate product ion for the precursor. If the first product ion has a measured retention time which is outside the range of T1+/− the expected error window or retention time window, then the first product ion is not considered as a candidate. The foregoing expected error window is also used in subsequent processing steps in connection with matching product ions to precursors in target injections when performing Venn intersection processing described herein. A target injection may refer to an injection of the input data other than the reference injection. Target injections may be used in producing the remaining spectra processed in the flowchart 1000 in the loop formed with a top testing step 1006.

At step 1006, a determination is made as to whether all the spectra in the input data set have been processed. If not, control proceeds to step 1010 where the variable current spectrum is assigned to the next spectrum in the input data set. At step 1012, the precursor and product ions for the current spectrum are determined. The current spectrum is searched for an ion having the same mass and retention time (within a second threshold or window) as the precursor of the reference spectrum. It should be noted that the product ions present in the reference spectrum also appear in the current spectrum.

An embodiment may also utilize the foregoing second threshold or window representing a window of time used when searching for a precursor having a particular mass in a target injection such as in step 1012 processing. For example, a precursor having a mass m1 at a retention time T1 may be determined in a reference injection. For a subsequent target injection, processing searches for an ion having the same mass m1 and a retention time of T1+/− the second window or threshold. The second threshold or window may be empirically determined and may vary in accordance with an embodiment. For example, an embodiment may assign an initial value to the second threshold, such as based on 2-3 chromatographic peaks widths. The second threshold may be modified or refined in accordance with empirical experimentation of a system. For example, if an embodiment utilizes a system or methodology introducing a large amount of error or noise, the second threshold or window may be increased.

In connection with step 1012 processing, it should also be noted that a precursor in the current spectrum is identified as being at a mass and is matched to the precursor in the reference or first spectrum of step 1004 having the same mass. A first mass of the precursor in the first spectrum may be deemed to be the same mass as a second mass of a precursor in the current spectrum if the first mass is within the specified mass tolerance of the second mass.

At step 1014, the precursor of the current spectrum may be time-aligned with the precursor of the reference spectrum and all product ions in the current spectrum are appropriately and accordingly time shifted. For example, if the retention time of the precursor in the reference spectrum is 10.0 minutes and the retention time of the precursor in the current spectrum is 9.8 minutes, the precursor and product ions in the current spectrum are shifted +0.2 minutes. Once the shifting is complete, control proceeds to step 1020 where the product ions in the current spectrum which are within the expected retention window of error or threshold tolerance are determined. At step 1020, the particular product ions which are within the expected window of error may be recorded for use in a later processing step.

It should be noted that the processing steps of flowcharts 1000 and 1050 set forth steps that may be used in specifying a predetermined number or portion of the spectra that a product ion must be included in to qualify as matching the precursor. The predetermined number or portion may be equal to, or less than, the total number of spectra in the input data set. For example, as described herein, an embodiment may specify a threshold or minimum number of spectra less than the total number in the input data set. If a candidate product ion is included in at least the specified threshold number of spectra within the expected window of error for a retention time of a precursor, then the candidate product ion may be determined as being associated with the precursor.

Control then proceeds from step 1020 to step 1006.

If the determination at step 1006 evaluates to yes, control proceeds to step 1051. In step 1051, a list of unique product ions in accordance with the predetermined mass tolerance window is determined. The product ions included in the first or reference spectrum and subsequent spectrum of the input data set as determined at step 1020 are examined. A first product ion in one spectrum having a first mass may be deemed as having a same mass as another product ion in a second spectrum if the first mass and the second mass are within the predetermined mass tolerance window. In connection with the techniques described herein, the first and second product ions may be deemed to be the same product ion in two different spectra. From step 1051, control proceeds to step 1052. For each product ion as determined in step 1051, the number of spectra from the input data set in which each product ion is determined as having a retention time of the precursor within the retention time window of error is tabulated. At step 1054, the current product ion variable is set to the first product ion. At step 1056, a determination is made as to whether the product ion has substantially the same retention time as the precursor (e.g., within the retention time window of error) for the threshold or predetermined number of spectra. In other words, if an embodiment specifies a threshold number of spectra at "M", it indicates that a product ion has to have a same retention time as the precursor within the retention time window for "M" spectra in order for step 1056 to evaluate to yes. If step 1056 evaluates to yes, control proceeds to step 1058 where the product ion is determined to be associated or matched with the precursor. From step 1058, control proceeds to step 1062. If step 1056 evaluates to no, control proceeds to step 1060 where the product ion is determined not to be associated or matched with the precursor.

Control proceeds to step 1062 where a determination is made as to whether all the candidate product ions have been processed. If so, control proceeds to step 1064 to generate an output spectrum. As described elsewhere herein, the output produced may be in a form other than a spectrum, such as an ion list. The output spectrum or other output generated in step 1064 may include the product ions determined to be associated with the precursor by having substantially the same retention time and peak shape as the precursor. As described herein, the product ions are candidates which have been determined in accordance with criteria including a threshold number of spectra from the input data set. If a candidate product ion is determined to have a retention time within a retention time's expected window of error for the threshold number of spectra, the candidate product ion is deemed to have the same retention time as a precursor with the retention time. If step 1062 evaluates to no, control proceeds to step 1066 where the current product ion variable is assigned to next product ion to be examined.

The techniques described herein will now be illustrated with additional figures. For the sake of simplicity of illustration, only a single precursor is illustrated although the techniques described herein may be used in connection with samples in which multiple precursors have a common retention time.

Figure 12:
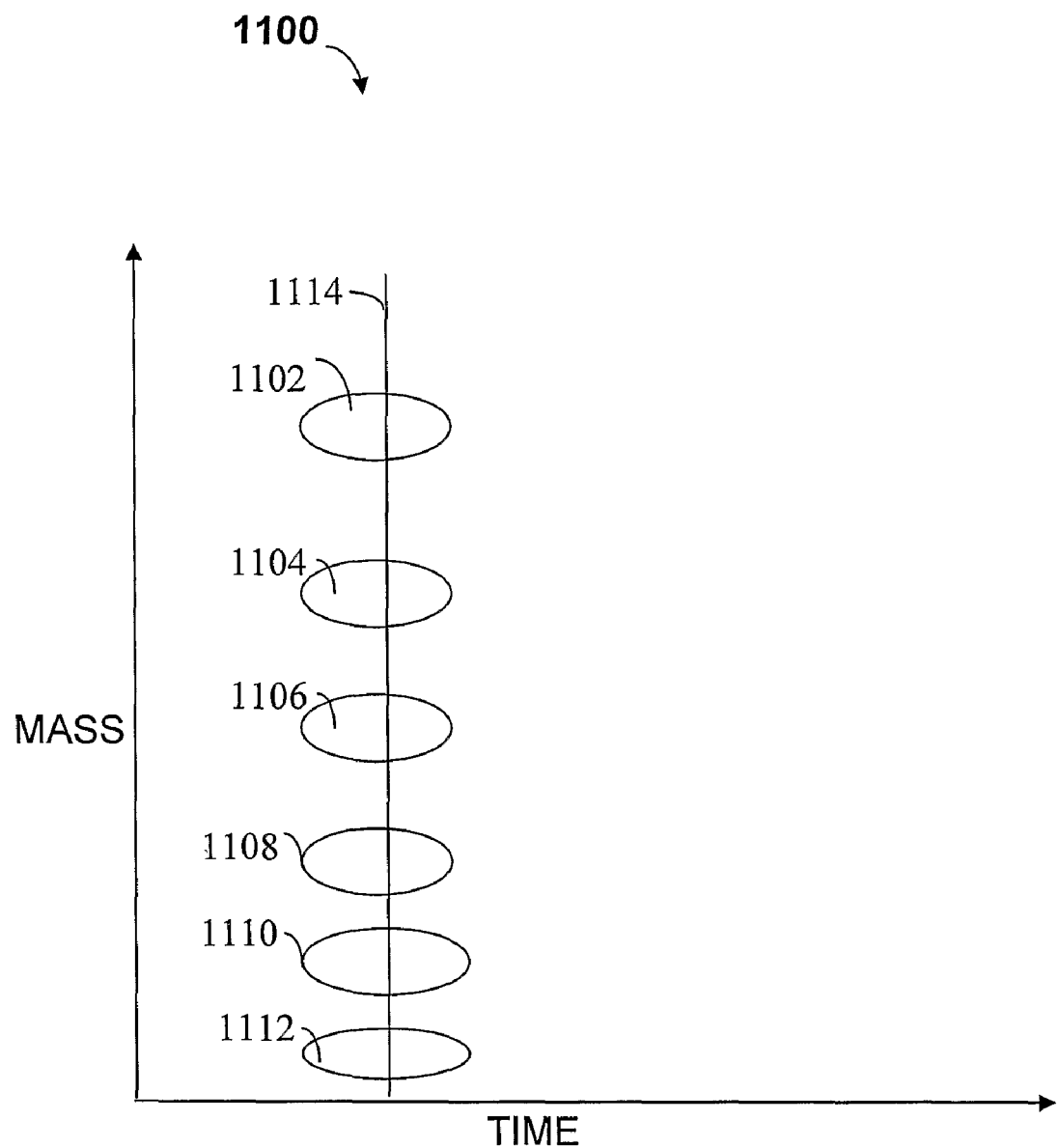
FIG. 12 is a graphical representation of a reference injection, in accordance with one embodiment of the invention.

Referring now to FIG. 12, shown is a graphical representation of a reference injection. In this example 1100, a precursor 1102 and product ions 1102, 1104, 1106, 1108, 1110 and 1112 have the retention time of 1102 as indicated by 1114. It should be noted that, all ions having a measured retention time within the retention time window of expected error are considered.

Figure 13A:
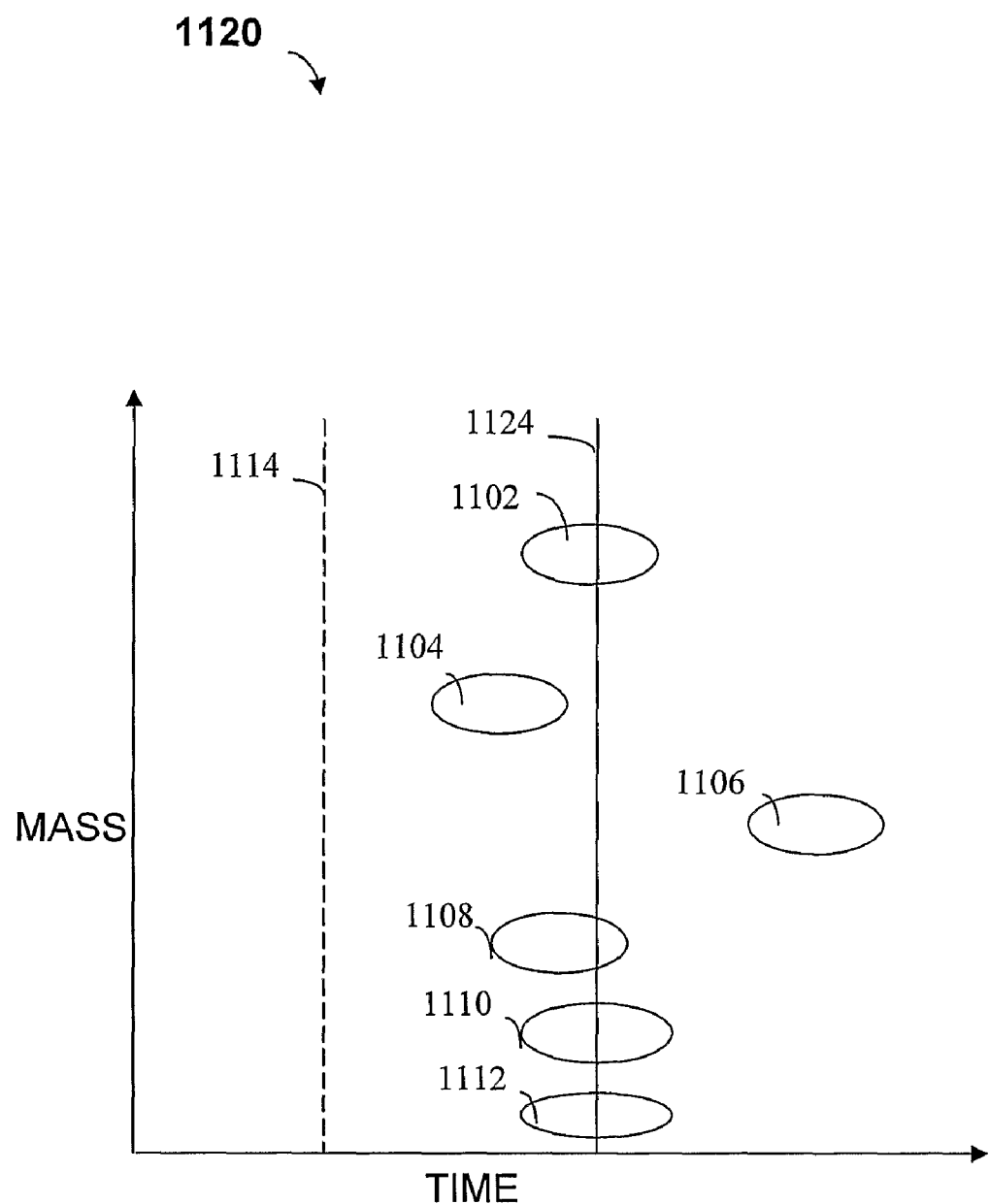
FIG. 13A is a graphical representation of a first target injection, in accordance with one embodiment of the invention.
Figure 13B:
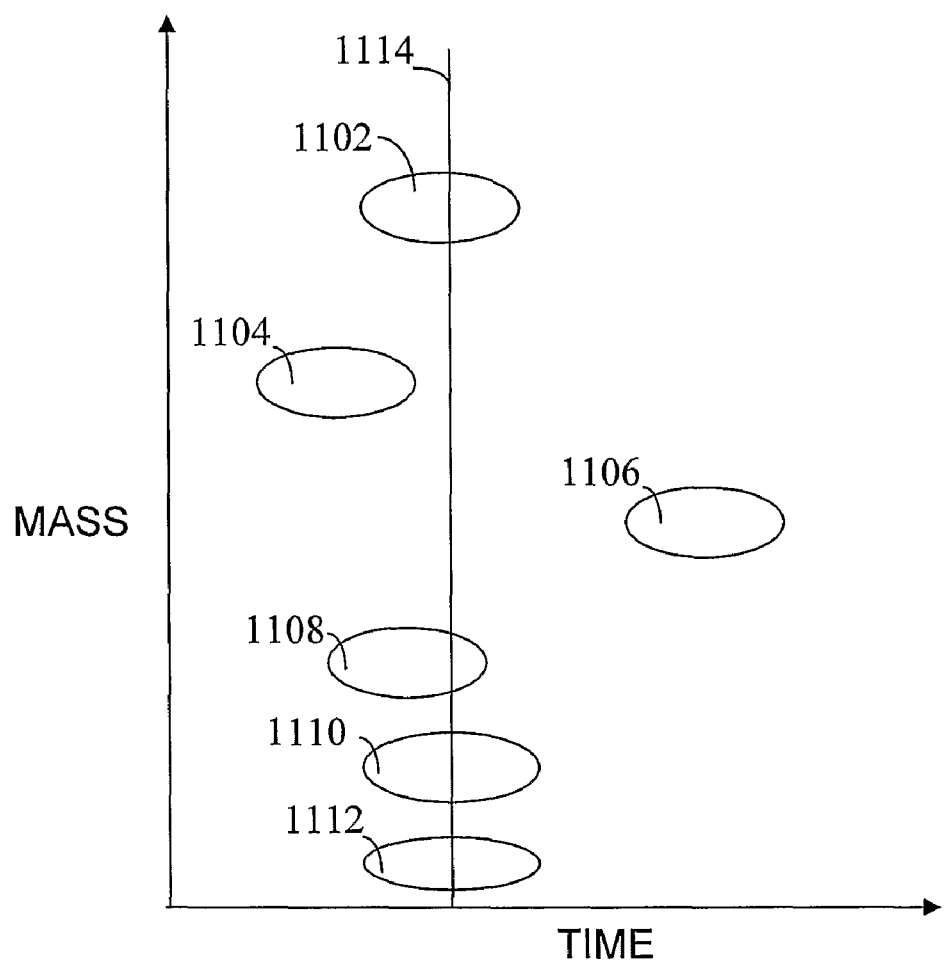
FIG. 13B is graphical representation of an alignment or normalization of the first target injection of FIG. 13A and the reference injection of FIG. 12 in accord with a common precursor.

Referring now to FIG. 13A, shown is a graphical representation of another injection. The injection of the example 1120 may be referred to as a first target injection. In this example 1120, the data for the target injection is searched for a retention time for the same mass as the precursor from the reference injection. The search for the retention time is performed with respect to the second threshold or predetermined window as described above. In the example 1120, the precursor 1102 is illustrated as having a retention time indicated by 1124. In FIG. 13B, shown is the alignment or normalization of the first target injection in accordance with the retention time of the precursor from the reference injection. The precursor from the reference injection and the first target injection are aligned. The product ions are also accordingly shifted. It should be noted that as described for the reference injection, the precursor of a target injection may be determined as those one or more ions having the greatest mass and intensity. In connection with the example 1124, note that product ions 1104 and 1106 do not have the same retention time of 1114 as the precursor. The remaining product ions 1108, 1110 and 1112 have the retention time 1114 within the expected window of error of the retention time.

Figure 14A:
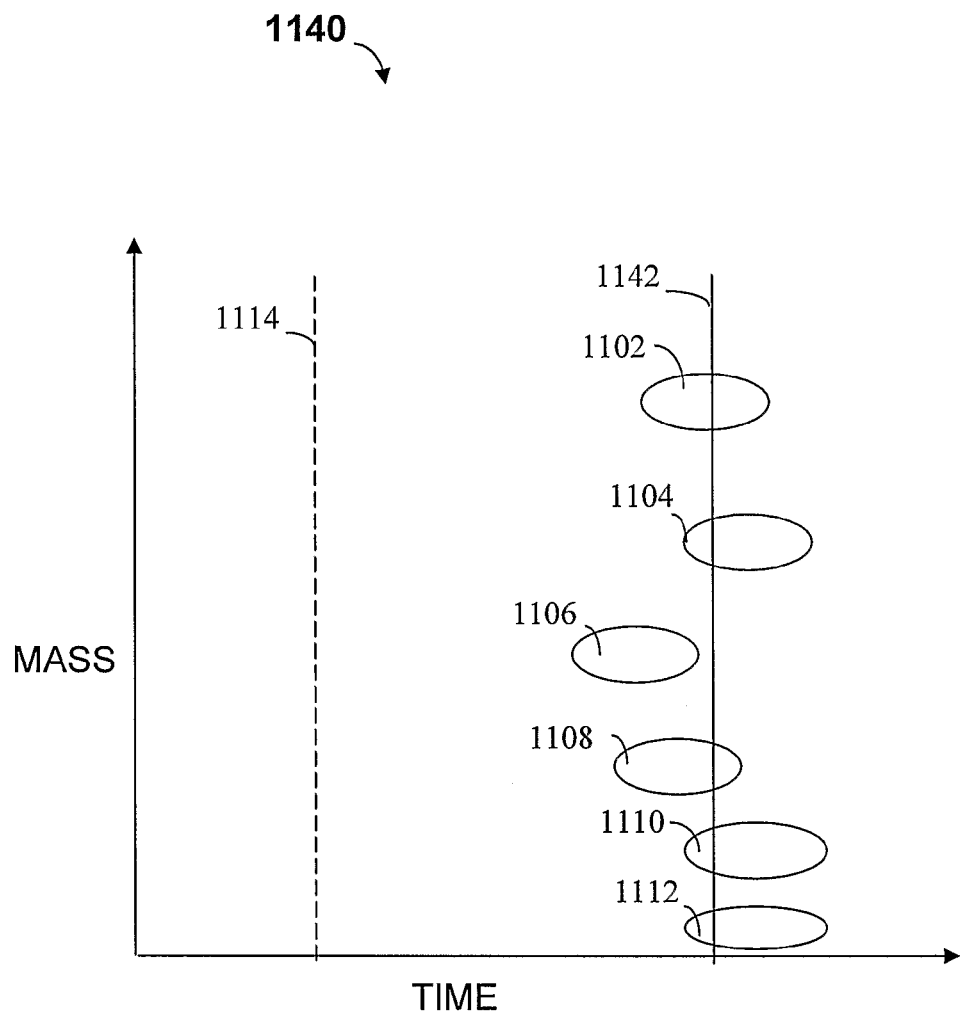
FIG. 14A, shown is a graphical representation of a second target injection.
Figure 14B:
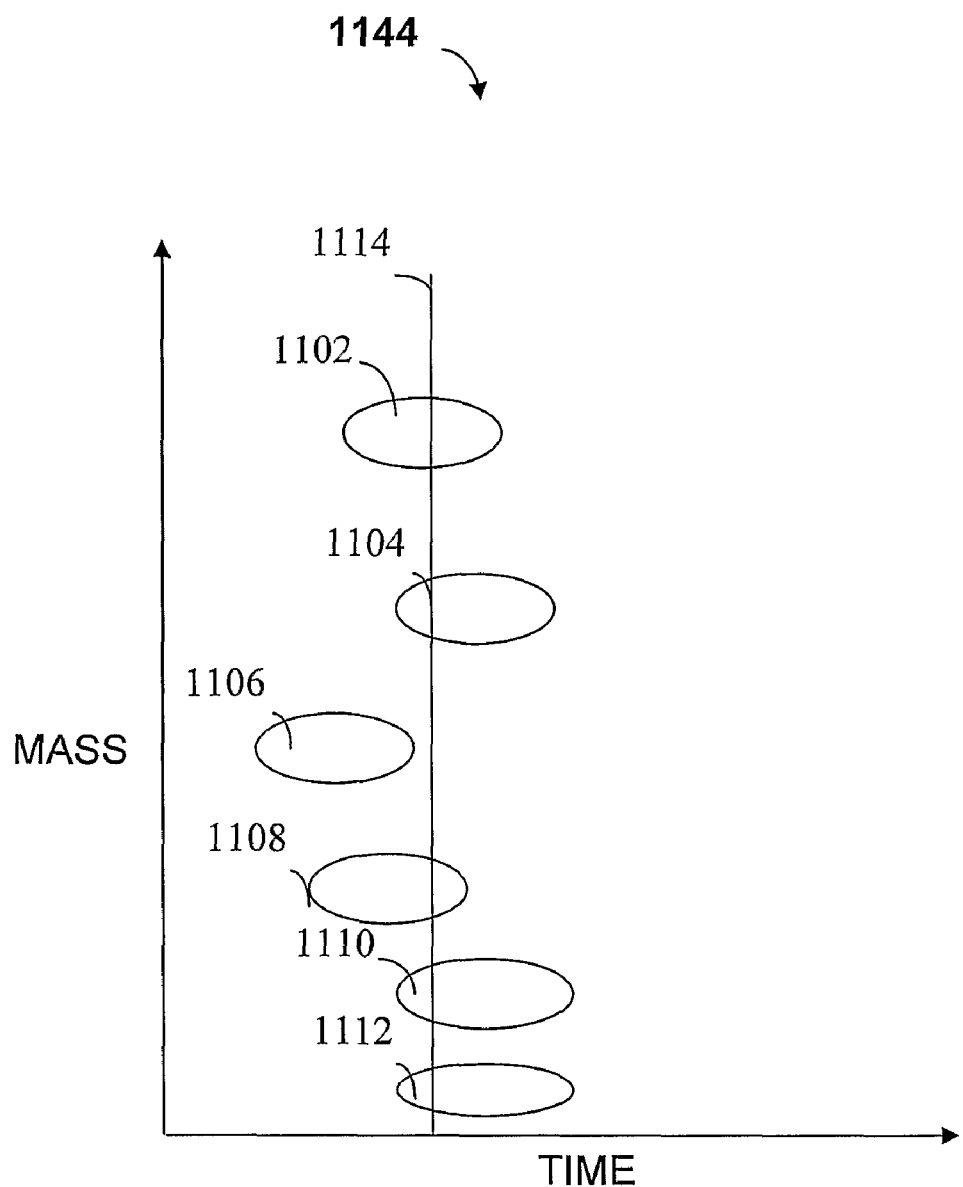
FIG. 14B is graphical representation of an alignment or normalization of the second target injection of FIG. 14A and the reference injection of FIG. 12 in accord with the common precursor.

Referring now to FIG. 14A, shown is a graphical representation of a second target injection. In this example 1140, the data for the second target injection is searched for a retention time for the same mass as the precursor from the reference injection in order to determine a precursor ion. The foregoing searching to determine the precursor ion is performed in a manner similar to as described in connection with FIG. 13A. In the example 1140, the precursor 1102 is illustrated as having a retention time of 1142 and substantially the same mass (e.g., within the mass tolerance) as the precursor 1102 in FIG. 13A. In FIG. 14B, shown is the alignment or normalization of the second target injection in accordance with the retention time of the precursor from the reference injection. The precursor from the reference injection and the second target injection are aligned at retention time 1114 and each of the product ions is also accordingly shifted. In the example 1144, note that product ion 1106 is illustrated as not having the retention time 1114 within a retention time window of expected error as may be determined, for example, using $+/-\frac{1}{10}^{th}$ the FWHM of the mass spectral peak as described elsewhere herein.

Figure 15:
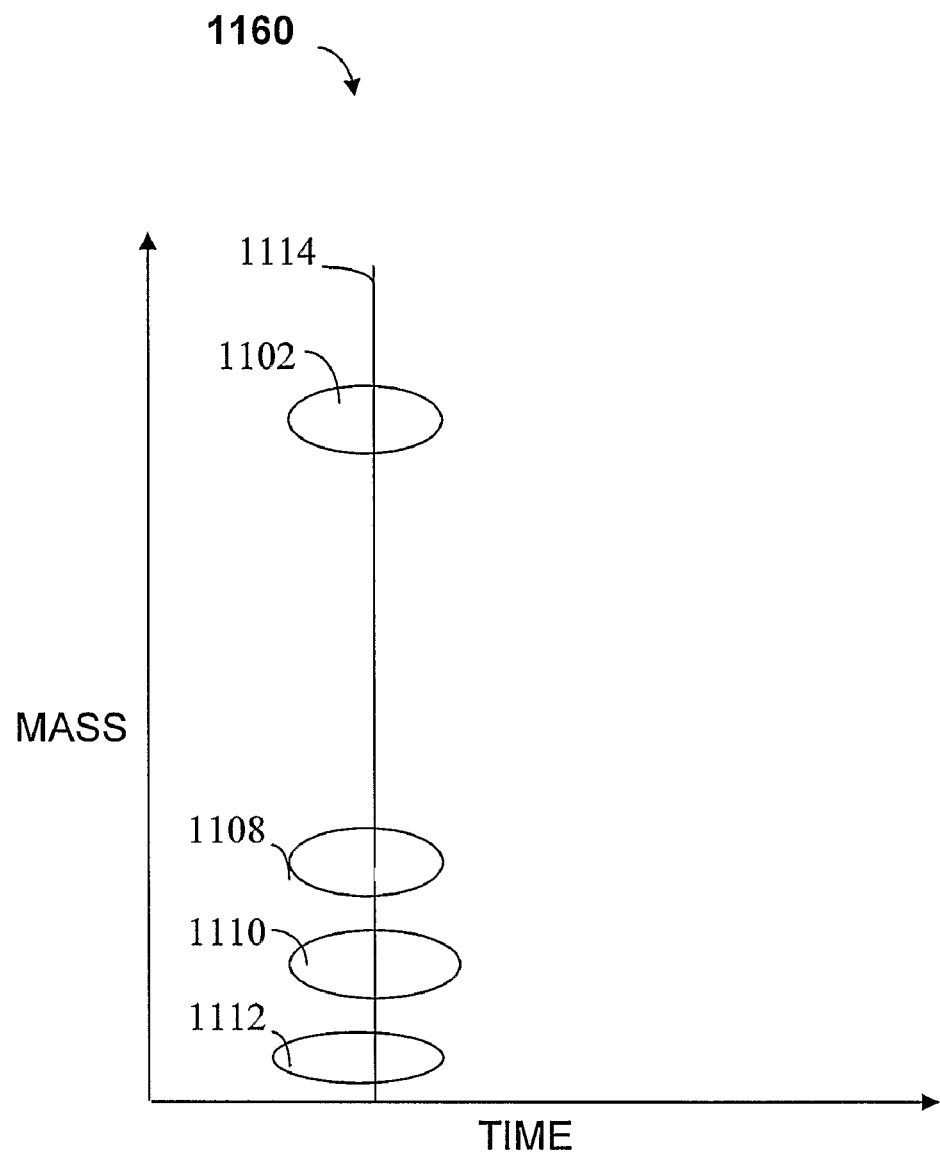
FIG. 15 is a graphical representation of an output spectrum including a precursor and associated product ions, in accordance with one embodiment of the invention.

An example of an output spectrum including the precursor and associated product ions as determined using the techniques described herein is illustrated in FIG. 15.

Based on the foregoing examples, it may be determined that only product ions 1108, 1110 and 1112 are matched or associated with the precursor ion 1102 having a retention time illustrated by 1122. Product ions 1104 and 1106 were not within the retention time window of expected error with respect to 1114 in the first target injection. Product ion 1106 was not within the retention time window of expected error with respect to 1114 in the second target injection.

The foregoing techniques for performing retention time matching may be used to annotate a database or catalog, such as a peptide catalog. As known in the art, for example, a protein sequence database may be initially obtained and stored on a data storage device. The database may be annotated using the techniques just described. The peptide database includes information such as what ions comprise a particular peptide. The techniques described herein may be used to annotate the database to further identify which of the ions of those listed in the database are used in connection with protein profiling, for example, to characterize or identify the protein. For example, there may be a peptide database which includes a protein and identifies the 20 tryptic peptides in the protein's sequence. It may be that only a portion, such as for example 10, of those 20 peptides are ionized and may be used as precursors to identify the protein. Using the techniques described herein, the peptide database may be annotated to denote the three most intense precursors of the 10. The three most intense precursors may be used to identify the protein as in connection with profiling as described elsewhere herein. The peptide database may be further annotated to identify the product ions for each of the precursors as also identified, for example, using the retention time matching technique with the Venn intersection processing as described herein.

In connection with an input data set in which a single spectrum has more than one precursor with a same retention time, a reference injection may be determined. Such a spectrum may be produced, for example, in connection with an analyzed complex sample. The mass of each precursor may be determined from the reference injection. As an example, let a first mass, m1, be associated with a first precursor and a second mass, m2, be associated with a second precursor. Multiple target injections may be examined with respect to each precursor. The target injections may be searched for an ion having the mass m1 and having a retention time within the specified second window or threshold. Such an ion is determined to be the first precursor in the target injection. A retention time for the first precursor in a target injection is determined and aligned with the retention time of the first precursor in the reference injection. Alignment and other processing steps may be performed as described herein for each of the target injections to determine which product ions are associated or matched with the first precursor. The same set of target injections may also be processed with respect to the second precursor having mass m2. In a manner similar to that as set forth regarding the first precursor with mass m1, the target injections may be searched for an ion having the mass m2 and having a retention time within the second window or threshold as described elsewhere herein. A retention time for the second precursor in a target injection is determined and aligned with the retention time of the second precursor in the reference injection. Alignment and other processing steps may be performed as described herein for each of the target injections to determine which product ions are associated or matched with the second precursor. As such, in each of the target injections, appropriate product ions occurring at substantially the same retention time as each of the precursors may be examined and processed.

To further illustrate the use of these techniques with a spectrum including more than one precursor, reference will be made to FIG. 16 and FIG. 17.

Figure 16:
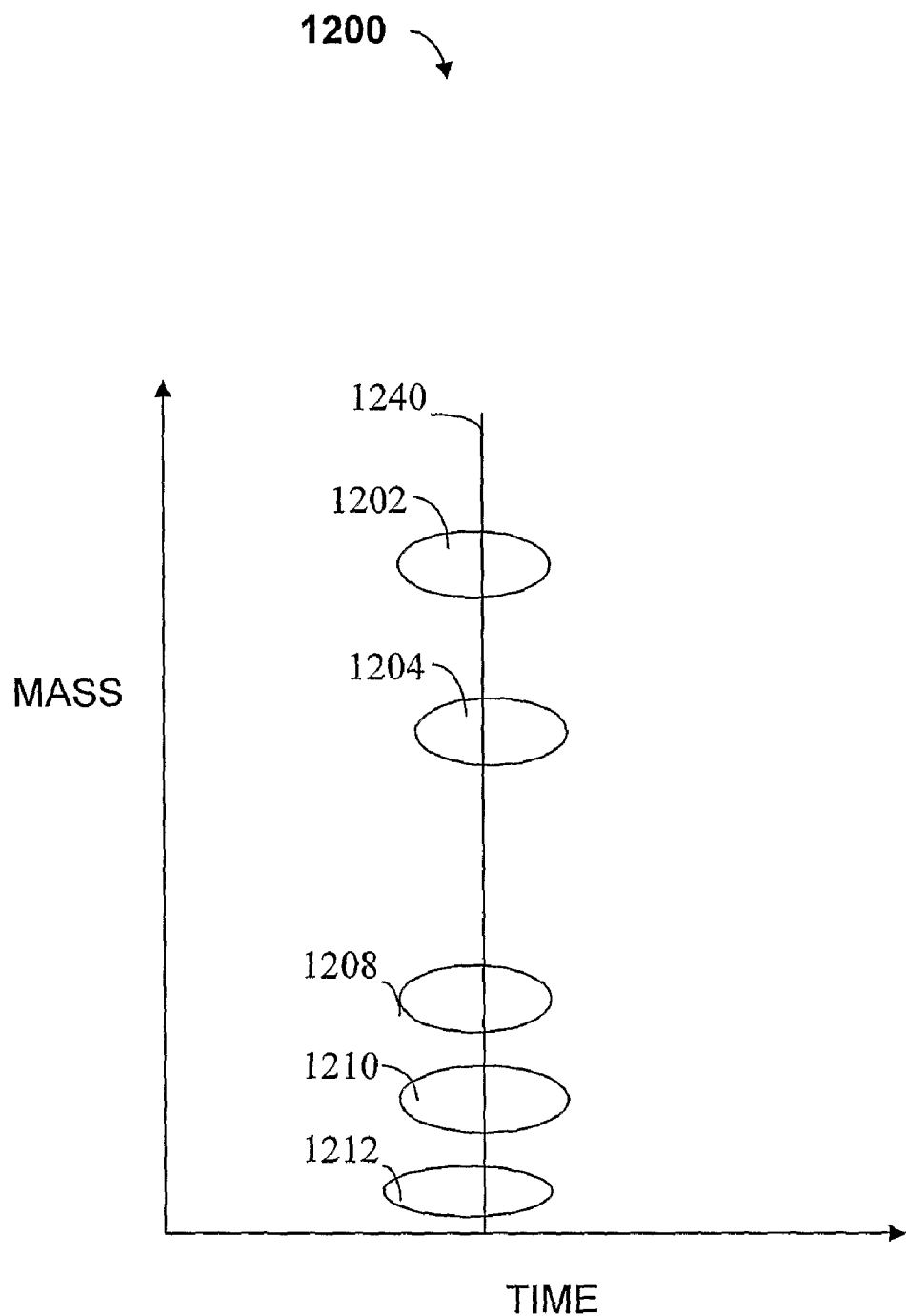
FIG. 16 is a graphical representation of a reference injection, in accordance with one embodiment of the invention.
Figure 17:
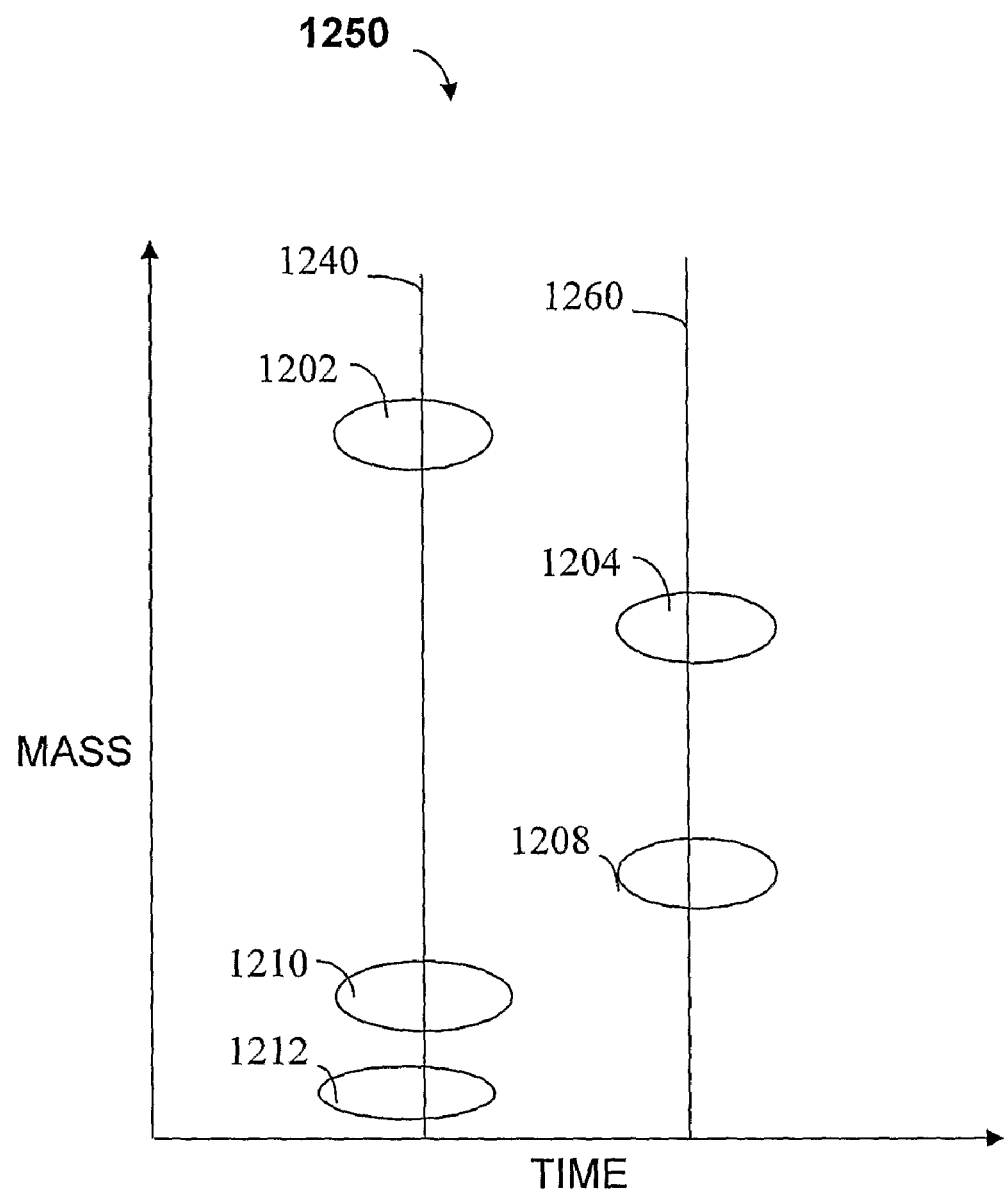
FIG. 17 is a graphical representation of a first target injection for analysis with the reference injection of FIG. 16.

In FIG. 16, shown is an example spectrum that may be produced for a reference injection. In the example 1200, it may be determined that element 1202 and 1204 are precursors having a retention time illustrated by 1240. Elements 1202 and 1204 may represent ions determined to be precursors in accordance with their large mass and intensity in relation to other ions 1208, 1210 and 1212. In the reference injection, it is not yet clear which product ions 1208, 1210 and 1212 may be associated with which precursor. A first target injection is graphically illustrated in FIG. 17. When performing processing of the first target injection for the precursor 1202, the first injection may be searched for an ion having the mass of 1202 and having a retention time within the second window or threshold of the retention time represented by 1240. In this first target injection, a precursor having the mass of 1202 also occurs at a retention time 1240. However, in this target injection, only product ions 1210 and 1212, not 1208, occur at the retention time 1240 within the specified window of expected error. As such, product ion 1208 may not be associated or matched with precursor 1202. When performing analysis using the first target injection with respect to precursor 1204, the first target injection is searched for an ion having the mass of 1204 and having a retention time within a specified window of the retention time represented by 1240. In this instance, an ion having the mass of 1204 occurs at retention time 1260. Only product ion 1208 occurs at retention time 1260 within the specified window of expected error. As such, product ions 1210 and 1212 may not be associated or matched with precursor 1204.

It should be noted that two precursors, as well as product ions, having different retention times may have a same measured retention time in one injection. However, the two precursors as well as their respective product ions will have different measured retention times outside of the window of error, such as the $1/10^{th}$ peak width in repeated experiments. Thus, a portion of ions which seemingly are related in a single injection may be shown to be unrelated through repeated experimentation.

It should be noted that a precursor ion and its one or more related product ions having a same retention time and peak shape may be referred to as a common retention time entity (CRTE). Using the techniques described herein for retention time matching, ions which seemingly are included in a single CRTE in a single injection can be shown to comprise two or more groupings or CRTEs based on different in retention times of subsequent injections.

As described herein, an embodiment may optionally perform processing of an input sample prior to processing by a mass spectrometer. Such processing may complement or replace separation by liquid chromatographic separation in an embodiment. In one embodiment, the sample may be a mixture of one or more molecules, such as peptides or proteins. Prior to performing mass spectroscopy, an embodiment may separate various proteins in the mixture using two-dimensional gel electrophoresis (2DE). The resulting spots may be excised and digested to break the proteins into shorter polypeptide chains. These digests may be analyzed via mass spectroscopy. In this particular example, the substance may be a mixture of one or more molecules, for example, such as peptides or proteins. An input sample or substance which includes proteins may be digested as part of enzymatic digestion processing. This enzymatic digestion processing is one type of separation processing that breaks the proteins in the sample into shorter polypeptide chains. Subsequently, the digests may then be further separated using another separation processing technique such as, for example, liquid chromatography (LC), as described above, 2D Gel separation, and the like. It should be noted that generally any separation technique and/or digestion technique may be used to separate the various polypeptides in accordance with, for example, molecular weight, electrical fields and the like. The foregoing separation may optionally be performed in an embodiment on a sample prior to undergoing mass spectroscopy and generated spectra or other forms of data that may be included in the input data set for retention time matching.

It should be noted that as used herein, two measured retention times may be characterized as substantially the same if two measured retention times are within the window of expected error such as described above for use in matching precursors with product ions. The precursor and the product ions may be deemed to have the same retention time even though the actual measured retention times may vary within the window of expected error.

It should also be noted that the techniques for retention time matching may be applied to samples which are processed using the fractionation techniques described herein, such as, for example, fractionation of a protein mixture.

The processing steps performed in an embodiment, such as illustrated in FIG. 10 and FIG. 11, may be performed as a result of code executed by a computer processor. The code may be stored on any one of a variety of different forms of computer readable media, memory and the like.

In connection with the techniques described herein in one embodiment, a molecule in a mixture may be separated in a liquid chromatograph and elute in an unmodified form. The foregoing molecule can give rise to one or more ions in an LC/MS system and may also be referred to as the originating molecule. When subjected to the electrospray or other ionization processing, as well as other optional processing as may be included in an embodiment, a resulting mass spectrum of the originating molecule may include more than one ion. Multiple ions can result from, for example, the isotopic distribution of the molecule, the different charge states produced by ionization, and/or fragmentation mechanism applied to the ions, or other modifications imposed subsequent to elution from the LC. Thus, an originating molecule may produce one or more ions. In connection with the techniques described herein, the peak shapes and retention times of ions that derive from the same originating molecule are identical having measurements including retention times which are deemed to be the same.

An ion list as described in connection with the techniques herein may include one or more rows of data. In one embodiment, each row in an ion list contains a retention time, mass/charge, and intensity describing an ion. The data about each ion in the ion list may be obtained using any one of a variety of different techniques. For example, the data about one or more of the ions may be obtained using the Bateman technique in the LE or HE mode. An ion list may also refer to a list of entities referred to herein as accurate-mass retention-time entities ("AMRTs"), where each row contains a retention time, mwHPlus, intensity, and charge state as may be obtained using LE or HE acquisition mode. AMRTs are described in more detail in "Quantitative Proteomic Analysis by Accurate Mass Retention Time Pairs" by Silva, et al., Anal. Chem., Vol. 77, pages 2187-2200 (2005).

A spectrum included in an input data set used in connection with the techniques described herein for retention time matching may contain a list of ions (or AMRTs), each described by an m/z (or mwHPlus) and an intensity. An embodiment may obtain a spectrum in the input data set using a first technique including data obtained in a single scan as collected by the mass spectrometer. In this case, the ion list for the spectrum corresponds to mass spectral peaks as may be viewed in the spectrum, and the retention time of the spectrum is the acquisition time of the spectral scan. Alternatively, a spectrum may be obtained by selecting a retention time and a retention time window, and collecting all ions from an ion list whose retention time falls within that window as described, for example, in PCT Patent Application No. PCT US2005/004180, filed on Feb. 11, 2005, titled Apparatus and Method for Identifying Peaks in Liquid Chromatography/Mass Spectrometry Data and for Forming Spectra and Chromatograms, by Gorenstein et al. The retention time of the spectrum may be determined to be, for example, the retention time that lies in the middle of the window represented as $+/-\frac{1}{10}$ of a chromatographic peak width measured at FWHM.

It should be noted that spectrum included in the input data set used in connection with the retention time matching techniques described herein may be filtered, for example, such as by removing ions (or AMRTS) whose masses or intensities fall outside of a particular range.

In connection with the retention matching techniques herein, the output spectrum may be generated in a form in accordance with one or more output rules. For example, as described herein, a product ion in a first spectrum may have a first measured mass and the same product ion in a second spectrum of the input data set may have a second measured mass. The first and second measured masses may be deemed to be the same mass if they are within a defined mass tolerance. In the output spectrum, the mass for the product ion may be output in accordance with a rule such as, for example, the mass output in the output spectrum may be the average of the first and second measured masses. The output spectrum may, for example, consist solely of masses obtained from either the first or the second spectrum. Other embodiments may use other techniques to determine the values included in the output spectrum.

The one or more spectra included in an input data set used with the retention matching techniques may come from a variety of different sources. As described above, a spectrum may be generated in a variety of different ways from one or more experiments. A spectrum or other form of data included in the input data set may also come from a database or other data store. For example, data from previous experiments may be stored in a data base. The previous experimental data from the database, alone or in combination with additional new data, may be included in an input data set. The data included in the database or other data store may include theoretical or simulated experimental data for use in connection with the techniques described herein. A spectrum, for example, acquired using data-dependent acquisition (DDA) of MS/MS spectra may be included.

In an embodiment in which the sample used to obtain an input data set is a complex mixture of proteins, ions from different proteins may overlap in retention time. For such data, the retention time matching techniques may be applied by selecting a most intense ion in a single injection, and forming a spectrum of all ions within a retention time window of that most intense ion. This most intense ion may then found in a subsequent injection of substantially the same mixture of proteins by matching masses and retention times for the precursor in both injections as described herein (e.g., masses of each injection within the specified mass tolerance, and retention times of each injection being within the second threshold or window as described above).

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

What is claimed is:

1. A method of matching a precursor ion with one or more related product ions comprising:
   providing a plurality of input data sets obtained from a plurality of injections, each of said plurality of input data sets including a precursor ion and one or more product ions;
   normalizing, using a processor, said plurality of input data sets in accordance with a single retention time for said precursor ion;
   for each of said plurality of input data sets, determining, using a processor, which product ions are within a predetermined retention time window with respect to said single retention time; and
   if a product ion is within the predetermined retention time window for a specified number of said plurality of input data sets, determining, using a processor, that said product ion is related to a precursor having said single retention time.

2. The method of claim 1, wherein each of said plurality of, input data sets includes a plurality of precursor ions, and said normalizing further includes:
   aligning each precursor ion in each of said plurality of input data sets at said single retention time and shifting in time the product ions in said each of said plurality of input data sets in accordance with an amount by which said each precursor ion is shifted by said aligning.

3. The method of claim 1, wherein said predetermined retention time window is determined using a width and a threshold.

4. The method of claim 3, wherein said width is a chromatographic peak width determined as a full width half maximum peak of a mass spectral peak of the precursor ion.

5. The method of claim 3, wherein said threshold is $1/10^{th}$ of said width, and said predetermined retention time window has a lower bound determined by subtracting said threshold from said width, and said predetermined retention'time window has an upper bound determined by adding said threshold to said width.

6. The method of claim 1, wherein said plurality of injections is three.

7. The method of claim 1, further comprising:
   annotating an existing data store with information about said precursor ion and said one or more product ions.

8. The method of claim 1, wherein said method finds sets of masses having a same mass value for said plurality of injections, and a same retention time within said predetermined retention time window within each injection.

9. The method of claim 8, wherein said sets of masses have different retention times in one or more of said plurality of injections.

10. The method of claim 1, further comprising:
performing a plurality of replicate injections using a same sample.

11. The method of claim 1, further comprising:
performing a plurality of injections wherein each of said plurality of injections utilizes a different sample.

12. The method of claim 1, wherein said plurality of input data sets are obtained using a sample that is a protein mixture.

13. The method of claim 1, wherein said plurality of input data sets are obtained using a sample that is a serum.

14. The method of claim 1, wherein said plurality of input data sets are obtained using a sample that is a tissue sample.

15. The method of claim 1, wherein said plurality of input data sets are obtained using a sample that includes a plurality of proteins.

16. The method of claim 1, wherein said plurality of input data sets are obtained using a sample that is a single polypeptide.

17. The method of claim 1, wherein a portion of said plurality of input data sets, are produced by mass analyzing said precursor ion by alternating between a first low fragmentation mode and a second high fragmentation mode and obtaining a first spectrum for said first low fragmentation mode and a second spectrum for said second high fragmentation mode.

18. The method of claim 17, wherein said plurality of input data sets are obtained using a sample that is a digested protein, and the method further comprising:
performing LC/MS on said digested protein.

19. The method of claim 17, said plurality of input data sets are obtained using a sample that does not include proteins.

20. The method of claim 1, wherein at least a portion of said plurality of input data sets are spectra.

21. The method of claim 1, wherein at least a portion of said plurality of input data sets are ion lists, each ion in said ion lists being annotated with information including a retention time, an intensity, and a mass or a mass to charge ratio for said each ion.

22. The method of claim 1, wherein at least a portion of said plurality of input data sets are produced using a data binning technique.

23. The method of claim 1, wherein said specified number of said plurality of input data sets is three.

24. The method of claim 1, wherein said specified number is less than all the input data sets in said plurality of input data sets.

25. The method of claim 1, wherein said specified number is all the input data sets in said plurality of inputs data sets.

26. The method of claim 1, wherein said plurality of input data sets are obtained using at least one sample including a first protein, and the method further comprising:
providing a catalog of protein profiles, each of said protein profiles defined by an identity of a protein, said catalog including a profile for said first protein; and
updating said catalog by adding information about said first protein, said information including data about said precursor ion and said one or more related product ions.

27. The method of claim 26, further comprising:
identifying one or more unknown proteins of an unknown sample using said catalog.

28. The method of claim 27, wherein said identifying' includes:
obtaining first data about said unknown sample; and
matching a portion of said first data with said data about said precursor ion and said one or more related product ions included in said catalog to identify said first protein as being included in said unknown sample.

29. The method of claim 1, wherein a first product ion in a first input data set having a first mass and a second product ion in a second input data set having a second mass are determined to be a same product ion if said first mass is within a predetermined mass tolerance window of said second mass.

30. An apparatus for analyzing a sample comprising:
a chromatography module;
a mass-spectrometry module in communication with said chromatography module; and
a control unit in communication with said chromatography module and said mass spectrometry module, said control unit including at least one processor and a memory for storing a plurality of instructions executed by said processor, said plurality of instructions causing said processor to perform:
providing a plurality of input data sets obtained from a plurality of injections, each of said plurality of input data sets including a precursor ion and one or more product ions;
normalizing said plurality of input data sets in accordance with a single retention time for said precursor ion;
for each of said plurality of input data sets, determining which product ions are within a predetermined retention time window with respect to said single retention time; and
if a product ion is within the predetermined retention time window for a specified number of said plurality of input data sets, determining that said product ion is related to a precursor having said single retention time.

31. A non-transitory computer readable medium comprising code stored thereon for matching a precursor ion with one or more related product ions, the non-transitory computer readable medium comprising code for:
providing a plurality of input data sets obtained from a plurality of injections, each of said plurality of input data sets including a precursor ion and one or more product ions;
normalizing said plurality of input data sets in accordance with a single retention time for said precursor ion;
for each of said plurality of input data sets, determining which product ions are within a predetermined retention time window with respect to said single retention time; and
if a product ion is within the predetermined retention time window for a specified number of said plurality of input data sets, determining that said product ion is related to a precursor having said single retention time.

* * * * *